(12) United States Patent
Chan et al.

(10) Patent No.: US 6,410,529 B1
(45) Date of Patent: Jun. 25, 2002

(54) PHENYL UREA AND PHENYL THIOUREA DERIVATIVES AS HFGAN72 ANTAGONISTS

(75) Inventors: George Chan, Wynnewood, PA (US); Amanda Johns, Bishop's Stortford (GB); Anthony Jurewicz, Royersford, PA (US); Roderick Alan Porter, Ashwell (GB); Katherine Widdowson, King of Prussia, PA (US)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/485,623

(22) PCT Filed: Aug. 13, 1998

(86) PCT No.: PCT/GB98/02437

§ 371 (c)(1),
(2), (4) Date: May 10, 2000

(87) PCT Pub. No.: WO99/09024

PCT Pub. Date: Feb. 25, 1999

(30) Foreign Application Priority Data

Aug. 14, 1997 (GB) .............................................. 9717178
Apr. 8, 1998 (GB) .............................................. 9807756

(51) Int. Cl.[7] .................. C07D 217/00; C07D 215/00; A61K 31/47

(52) U.S. Cl. ............................... 514/233.5; 514/252.01; 514/307; 514/311; 546/146; 546/167; 544/128; 544/235

(58) Field of Search ................................. 514/307, 311, 514/233.5, 252.01; 546/146, 167; 544/128.235

(56) References Cited

U.S. PATENT DOCUMENTS

| 4,009,020 A | 2/1977 | Starke et al. ................ 504/178 |
| 5,552,411 A | 9/1996 | Downing et al. ........... 514/312 |
| 5,731,315 A | 3/1998 | Ewing et al. ................ 514/269 |

FOREIGN PATENT DOCUMENTS

| WO | WO 98/25611 | 6/1998 |

OTHER PUBLICATIONS

Nikolic, K., Chem. Abstracts, 1968, vol. 69, No. 8, Abstract No. 30159a.

*Primary Examiner*—Zinna Northington Davis
(74) *Attorney, Agent, or Firm*—Kathryn Sieburth; Mary E. McCarthy; Charles M. Kinzig

(57) ABSTRACT

Phenyl urea and phenylthiourea derivatives, processes for their production and their uses as pharmaceuticals are disclosed.

12 Claims, No Drawings

US 6,410,529 B1

PHENYL UREA AND PHENYL THIOUREA DERIVATIVES AS HFGAN72 ANTAGONISTS

This application is a §371 of PCT/GB98/02437, filed Aug. 13, 1998.

This invention relates to phenyl urea and phenyl thiourea derivatives and their use as pharmaceuticals It is well established that many medically significant biological processes are mediated by proteins participating in signal transduction pathways that involve G-proteins and/or second messengers, e.g. cAMP (Letkowitz, *Nature*, 1991, 351:353–354). Examples of these proteins include the GPC receptors, such as those for adrenergic agents and dopamine (Kobilka B. K. et al, *Proc. Natl Acad Sci.*, USA, 1987, 84:46–50; Kobila B. K. et at, *Science*, 1987, 238:650–656; Bunzow, J. R. et al, *Nature*, 1988, 336:783–787), G-proteins themselves, effector proteins, e.g. phospholipase C, adenyl cyclase, and phosphodiesterase, and actator proteins, e.g. protein kinase A and protein kinase C (Simon, M. I. et al, *Science*, 1991, 252:802–8).

The membrane protein gene superfamily of G-protein coupled receptors has been characterised as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuro-receptors.

G-protein coupled receptors have been characterised as including these seven conserved hydrophobic stretches of about 20 to 30 amino acids, connecting six divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1, rhodopsins, odorant, and cytomegalovirus receptors.

Polypeptides and polynucleotides encoding the human 7-transmembrane G-protein coupled neuropeptide receptor, HFGAN72, have been identified and are disclosed in U.S. Ser. Nos. 08/846,704 and 08/846,705, both of which were filed on Apr. 30, 1997, as well as in WO 96/34877.

Polypeptides and polynucleotides encoding polypeptides which are ligands for the HFGAN72 receptor are disclosed in U.S. Ser. No. 08/939,093 filed Jul. 2, 1997, U.S. Ser. No. 08/820,519 filed Mar. 19, 1997 and U.S. Ser. No. 08/033,604 filed Dec. 17, 1996.

HFGAN72 receptors are found in the mammalian host and, thus, may be responsible for many biological functions, including many pathologies including, but not limited to, depression; anxiety; obsessive compulsive disorder, affective neurosis/disorder; depressive neurosis/disorder, anxiety neurosis; dysthymic disorder; behaviour disorder; mood disorder; sexual dysfunction; psychosexual dysfunction; sex disorder; sexual disorder; schizophrenia; manic depression; delerium; dementia; severe mental retardation and dyskinesias such as Huntington's disease and Gilles de la Tourett's syndrome; disturbed biological and circadian rhythms; feeding disorders, such as anorexia, bulimia, cachexia, and obesity; diabetes; asthma; cancer; Parkinson's disease; Cushing's syndrome/disease; basophil adenoma; prolactinoma; hyperprolactinemia; hypopituitarism; hypophysis tumor/adenoma; hypothalamic diseases; Froehlich's syndrome; adrenohypophysis disease; hypophysis disease; hypophysis tumor/adenoma; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; disturbed biological and circadian rhythms; and sleep disturbances associated with such diseases as neurological disorders, neuropathic pain and restless leg syndrome, heart and lung diseases, mental illness such as depression or schizophrenia, and addictions; acute and congestive heart failue; hypotension; hypertension; urinary retention; osteoporosis; angina pectoris; myocardial infarction; ulcers; allergies; benign prostatic hypertrophy; chronic renal failure; renal disease; impaired glucose tolerance; migraine; hyperalgesia; pain; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g. HIV, post-polio syndrome, and post-herpetic neuralgia; phantom limb pain; labour pain; cancer pain; post-chemotherapy pain; post-stroke pain; post-operative pain; neuralgia; and tolerance to narcotics or withdrawal from narcotics; sleep disorders; sleep apnea; narcolepsy; insomnia; parasomnia; jet-lag syndrome; and other neurodegenerative disorders, which includes nosological entities such as disinhibition-dementia-parkinsonism-amyotrophy complex; pallido-ponto-nigral degeneration, epilepsy, and seizure disorders.

Experiments have shown that central administration of Lig 72A for the HFGAN72 receptor (Lig 72A is described in more detail below) stimulated food intake in freely-feeding rats during a 4 hour time period. This increase was approximately four-fold over control rats receiving vehicle. These data suggest that Lig 72A may be an endogenous regulator of appetite. Therefore, antagonists of its receptor may be useful in the treatment of obesity and diabetes, see *Cell*, 1998, 92, 573–585.

There is a significant incidence of obesity in westernised societies. According to WHO definitions a mean of 35% of subjects in 39 studies were overweight and a furter 22% clinically obese. It has been estimated that 5.7% of all healthcare costs in the USA are a consequence of obesity. About 85% of Type 2 diabetics are obese, and diet and exercise are of value in all diabetics. The incidence of diagnosed diabetes in westernised countries is typically 5% and there are estimated to be an equal number undiagnosed. The incidence of both diseases is rising, demonstrating the inadequacy of current treatments which may be either ineffective or have toxicity risks including cardiovascular effects. Treatment of diabetes with sulfonylureas or insulin can cause hypoglycaemia, whilst metformin causes GI side-effects. No drug treatment for Type 2 diabetes has been shown to reduce the long-term complications of the disease. Insulin sensitisers will be useful for many diabetics, however they do not have an anti-obesity effect.

Rat sleep/EEG studies have also shown that central administration of LIG72A, an agonist of HFGAN72 receptors, causes a dose-related increase in arousal, largely at the expense of a reduction in paradoxical sleep and slow wave sleep 2, when administered at the onset of the normal sleep period. Therefore antagonists of its receptor may be useful in the treatment of sleep disorders including insomnia The present invention provides phenyl urea and phenyl thiourea derivatives which are non-peptide antagonists of the human HFGAN72 receptor. In particular, these compounds are of potential use in the treatment of obesity including obesity observed in Type 2 (non-insulin-dependent) diabetes patients and/or sleep disorders.

Several phenyl urea derivatives are known in the literature, viz:

WO 93/18028 discloses the compound N-1-isoquinolinyl-N'-(1-methyl-1H-indol-5-yl)urea;

DE 2928485 discloses the compounds N-(3-chloro-4-trifluoromethylphenyl)-N'-4-quinolinylurea, and N-(3-chloro-4-trifluoromethylphenyl)-N'-(5-nitro-4-quinolinyl) urea;

DE 2801187 discloses the compound N-(3,4,5-trimethoxyphenyl)-N'-(7-chloro-4-quinolinyl)urea; and U.S. Pat. No. 3,406,176 discloses the compounds N-(4-methoxyphenyl)-N'-(7-chloro-4-quinolinyl)urea, and N-(4-chlorophenyl)-N'-(7-chloro-4-quinolinyl)urea;

none of these documents suggest the use of phenyl urea derivatives as HFGAN72 receptor antagonists.

According to the present invention there is provided a compound of formula (I):

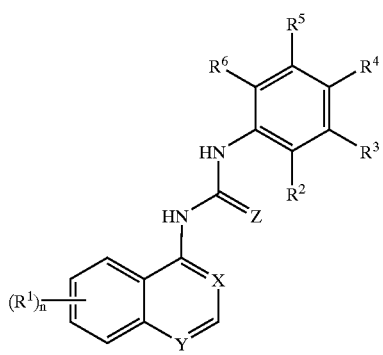

(I)

in which:
X and Y independently represent CH or nitrogen, provided that X and Y do not both represent CH;
Z represents oxygen or sulphur,
$R^1$ represents $(C_{1-6})$alkyl, $(C_{2-6})$alkenyl or $(C_{1-6})$alkoxy, any of which may be optionally substituted; halogen, $R^7CO$— or $NR^8R^9CO$—;
$R^2$, $R^3$, $R^4$, $R^5$ and $R^6$ independently represent $(C_{1-6})$alkyl, $(C_{2-6})$alkenyl, $(C_{1-6})$alkoxy or $(C_{1-6})$alkylthio, any of which may be optionally substituted; hydrogen, halogen, nitro, cyano, aryloxy, aryl$(C_{1-6})$alkyloxy, aryl $(C_{1-6})$alkyl, $R^7CO$—, $R^7SO_2NH$—, $R^7CON(R^{10})$—, $NR^8R^9$—, $NR^8R^9CO$—, —$COOR^8$ or heterocyclyl; provided that at least one of $R^2$, $R^3$, $R^4$, $R^5$ and $R^6$ is other than hydrogen;
or an adjacent pair of $R^2$, $R^3$, $R^4$, $R^5$ and $R^6$ together with the carbon atoms to which they are attached form an optionally substituted carbocyclic or heterocyclic ring;
$R^7$ is $(C_{1-6})$alkyl or aryl;
$R^8$ and $R^9$ independently represent hydrogen, $(C_{1-6})$alkyl, aryl or aryl$(C_{1-6})$alyl;
$R^{10}$ is hydrogen or $(C_{1-6})$alkyl; and
n is 0, 1, 2, 3 or 4;
or a pharmaceutically acceptable salt thereof;
provided that the compound is not:

a) N-1-isoquinolinyl-N'-(1-methyl-1H-indol-5-yl)urea;
b) N-(3-chloro-4-trifuoromethylphenyl)-N'-4-quinolinylurea;
c) N-(3-chloro-4-trifluoromethylphenyl)-N'-(5-nitro-4-quinolinyl)urea;
d) N-(3,4,5-trimethoxyphenyl)-N'-(7-chloro-4-quinolinyl) urea;
e) N-(4-methoxyphenyl)-N'-(7-chloro-4-quinolinyl)urea; or
f) N-(4-chlorophenyl)-N'-(7-chloro-4-quinolinyl)urea In formula (I) X preferably represents CH, Y preferably represents nitrogen and Z preferably represents oxygen.

When a halogen atom is present in the compound of formula (I) this may be fluorine, chlorine, bromine or iodine.

n is preferably 0 or 1.

When Y is nitrogen and n is 1, the group $R^1$ is preferably in the 6- or 8-position, particularly the 6-position.

$R^1$ is preferably halogen e.g. fluoro, or $(C_{1-6})$alkoxy e.g. methoxy. $R^1$ is most preferably fluoro.

When any one of $R^1$ to $R^6$ comprise a $(C_{1-6})$alkyl group, whether alone or forming part of a larger group, e.g. alkoxy or alkylthio, the alkyl group may be straight chain or branched, it preferably contains 1 to 4 carbon atoms and is most preferably methyl or ethyl.

When any one of $R^1$ to $R^6$ comprise a $(C_{2-6})$alkenyl group, whether alone or forming part of a larger group, the alkenyl group may be straight chain or branched, it preferably contains 2 to 4 carbon atoms and is most preferably allyl.

Suitable optional substituents for $(C_{1-6})$alkyl, $(C_{2-6})$alkenyl, $(C_{1-6})$alkoxy and $(C_{1-6})$alkylthio groups include one or more substituents selected from halogen e.g. fluoro, $(C_{1-4})$alkoxy e.g. methoxy, hydroxy, carboxy and $(C_{1-6})$alkyl esters thereof, amino, mono- or di-(C1–6)alkylamino and cyano.

When used herein the term "aryl", whether alone or forming part of a larger group, includes optionally substituted aryl groups such as phenyl and naphthyl, preferably phenyl. The aryl group may contain up to 5, more preferably 1, 2 or 3 optional substituents. Examples of suitable substituents for aryl groups include halogen, $(C_{1-4})$alkyl e.g. methyl, $(C_{1-4})$haloalkyl e.g. trifluoromethyl, $(C_{1-4})$alkoxy e.g. methoxy, $(C_{1-4})$alkoxy$(C_{1-4})$alkyl e.g. methoxymethyl, hydroxy, carboxy and $(C_{1-6})$alkyl esters thereof, amino, nitro, arylsulphonyl e.g. p-toluenesulphonyl, and $C_{1-4}$ alkylsulphonyl e.g. methanesulphonyl.

When any one of $R^2$ to $R^6$ represent heterocyclyl, this group is preferably a 5- to 10-membered monocyclic or bicyclic ring, which may be saturated or unsaturated, for example containing 1, 2 or 3 heteroatoms selected from oxygen, nitrogen and sulphur; for example pyrrolidine, oxazole, morpholine, pyrimidine or phthalimide. A ring containing one or two nitrogen atoms is especially preferred. The heterocyclyl group may contain up to 5, more preferably 1, 2 or 3 optional substituents. Examples of suitable substituents for heterocyclyl groups include halogen, $(C_{1-4})$alkyl e.g. methyl, $(C_{1-4})$haloalkyl e.g. trifluoromethyl, $(C_{1-4})$alkoxy e.g. methoxy, $(C_{1-4})$alkoxy$(C_{1-4})$alkyl e.g. methoxymethyl, hydroxy, carboxy, amino, nitro, arylsulphonyl e.g. p-toluenesulphonyl, and $(C_{1-4})$alkylsulphonyl e.g. methanesulphonyl.

When an adjacent pair of $R^2$ to $R^6$ together with the carbon atoms to which they are attached form a carbocyclic or heterocyclic ring it is preferably a 5- to 7-membered ring, which may be aromatic or non-aromatic. Heterocyclic rings preferably contain 1, 2 or 3 heteroatoms selected from oxygen, nitrogen and sulphur; for example oxazole, imidazole, thiophene, pyran, dioxan, pyrrole or pyrrolidine. A ring containing one nitrogen atom and one oxygen atom is preferred. It is particularly preferred for the nitrogen to be attached directly to the $R^4$ position. A carbocyclic or heterocyclic ring formed by an adjacent pair of $R^2$ to $R^6$ together with the carbon atoms to which they are attached may be optionally substituted on carbon or nitrogen by one or more substituents, e.g. up to 3 substituents. Examples of suitable substituents for the carbocyclic or heterocyclic ring include =O, $(C_{1-4})$alkyl e.g. methyl, aryl$(C_{1-4})$alkyl e.g. benzyl or 3-phenylpropyl, aryl e.g. phenyl, $(C_{1-4})$alkoxy, $(C_{1-4})$alkoxy$(C_{1-4})$alkyl e.g. methoxymethyl, hydroxy, hydroxy$(C_{1-4})$alkyl e.g. hydroxyethyl, $R^aCO_2$—, $R^aCO_2$($C_{1-4}$)alkyl e.g. carboethoxypropyl, cyano, cyano($C_{1-4}$)alkyl e.g. 3-cyanopropyl, $R^aR^bN$ and $R^aR^bN(C_{1-4})$alkyl; in which $R^a$ and $R^b$ are independently selected from hydrogen and $(C_{1-4})$alkyl.

A preferred group of compounds are those in which $R^2$ to $R^6$ independently represent hydrogen, halogen, $(C_{1-6})$alkoxy e.g. methoxy, $(C_{1-6})$alkylthio e.g. methylthio, or $NR^8R^9$ wherein $R^8$ and $R^9$ preferably represent $(C_{1-6})$alkyl e.g. dimethylamino, and at least one of $R^2$ to $R^6$ is other than hydrogen; or an adjacent pair of $R^2$ to $R^6$ together with the carbon atoms to which they are attached form an optionally substituted 5- to 7-membered heterocyclic ring, e.g. a 6 or 7-membered non-aromatic heterocyclic ring or a 5- or 6-membered aromatic heterocyclic ring.

A further preferred group of compounds are those in which $R^2$, $R^5$ and $R^6$ represent hydrogen.

A further preferred group of compounds are those in which $R^2$, $R^4$ and $R^6$ represent hydrogen.

A preferred group of compounds are those in which either $R^3$ and $R^4$, or $R^3$ and $R^5$ are other than hydrogen.

A group of compounds according to the invention which may be mentioned are the compounds of formula (Ia):

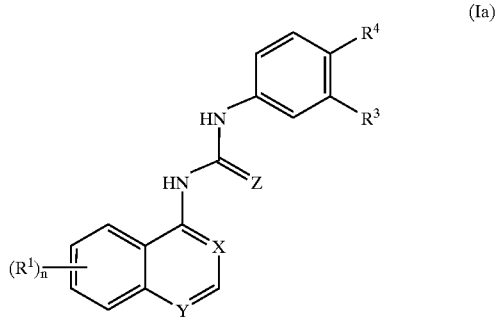

(Ia)

in which:
X and Y independently represent CH or nitrogen, provided that X and Y do not both represent CH;
Z represents oxygen or sulphur,
$R^1$ represents halogen or $(C_{1-6})$alkoxy;
$R^3$ and $R^4$ independently represent hydrogen, halogen, nitro, cyano, $(C_{1-6})$alkyl, $(C_{1-6})$alkoxy, aryloxy, $CF_3O$, $(C_{1-6})$alkylthio, amino, mono- or di-$(C_{1-6})$alkylamino, monoarylamino, mono$(C_{1-6})$alkylarylamino, $R^7CO$—, $R^7SO_2NH$—, $R^7CON(R^{10})$—, $NR^8R^9CO$— or heterocyclyl;
or $R^3$ and $R^4$ together with the carbon atoms to which they are attached form an optionally substituted carbocyclic or heterocyclic ring;
$R^7$ is $(C_{1-6})$alkyl or aryl;
$R^8$ and $R^9$ independently represent hydrogen, $(C_{1-6})$alkyl, aryl or $(C_{1-6})$alkylaryl;
$R^{10}$ is hydrogen or $(C_{1-6})$alkyl; and
n is 0, 1, 2 or 3;
or a pharmaceutically acceptable salt thereof.

Another group of compounds according to the invention which may be mentioned are the compounds of formula (Ib):

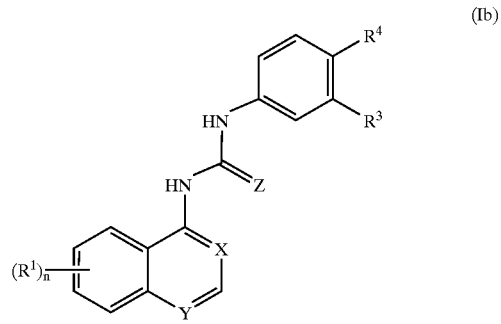

(Ib)

in which:
X and Y independently represent CH or nitrogen, provided that X and Y do not both represent CH;
Z represents oxygen or sulphur;
$R^1$ represents halogen or $(C_{1-6})$alkoxy;
$R^3$ and $R^4$ independently halogen or $(C_{1-3})$alkoxy or together with the carbon atoms to which they are attached form an optionally substituted heterocyclic ring; and
n is 0, 1, 2 or 3;
or a pharmaceutically acceptable salt thereof.

Particular compounds according to the invention include those mentioned in the examples and their pharmaceutically acceptable salts.

It will be appreciated that for use in medicine the salts of the compounds of formula (I) should be pharmaceutically acceptable. Suitable pharmaceutically acceptable salts will be apparent to those skilled in the art and include for example acid addition salts formed with inorganic acids e.g. hydrochloric, hydrobromic, sulphuric, nitric or phosphoric acid; and organic acids e.g. succinic, maleic, acetic, fumaric, citric, tartaric, benzoic, p-toluenesulphonic, methanesulphonic or naphthalenesulphonic acid. Other salts e.g. oxalates, may be used, for example in the isolation of compounds of formula (I) and are included within the scope of this invention. Also included within the scope of the invention are solvates and hydrates of compounds of formula (I).

The invention extends to all isomeric forms including stereoisomers and geometric isomers of the compounds of formula (I) including enantiomers and mixtures thereof e.g. racemates. The different isomeric forms may be separated or resolved one from the other by conventional methods, or any given isomer may be obtained by conventional synthetic methods or by stereospecific or asymmetric syntheses.

According to a further feature of the invention we provide a process for the preparation of the compounds of formula (I) and salts thereof which comprises coupling a compound of formula (II);

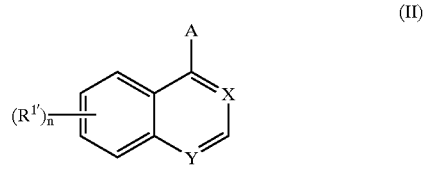

(II)

with a compound of formula (III);

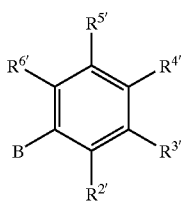

(III)

wherein A and B are appropriate functional groups to form the —NHCONH— or —NHCSNH— moiety when coupled; X, Y and n are as defined in formula (I); and $R^{1'}$ to $R^{6'}$ are $R^1$ to $R^6$ as defined in formula (I) or groups convertible thereto; and thereafter optionally and as necessary and in any appropriate order, converting any $R^{1'}$ to $R^{6'}$ when other than $R^1$ to $R^6$ respectively to $R^1$ to $R^6$, and/or forming a pharmaceutically acceptable salt thereof.

Suitable examples of groups A and B are:
(i) A is —$CON_3$ and B is —$NH_2$
(ii) A is —$NH_2$ and B is —$NH_2$
(iii) A is —$CO_2H$ and B is —$NH_2$
(iv) A is —N═C═O and B is —$NH_2$
(v) A is —$NH_2$ and B is —N═C═O
(vi) A is —N═C═S and B is —$NH_2$
(vii) A is —$NH_2$ and B is —N═C═S
(viii) A is —NHCOL and B is —$NH_2$
(ix) A is —$NH_2$ and B is —NHCOL
(x) A is halogen and B is —$NHCONH_2$.

Wherein L is a leaving group such as chloro or bromo, imidazole or phenoxy or phenylthio optionally substituted for example with halogen, for example chlorine.

When A and B are both $NH_2$, the reaction is generally effected in the presence of a urea coupling agent such as carbonyldiimidazole.

When A is —$CO_2H$ and B is —$NH_2$ the reaction is generally effected in the presence of an agent such as diphenylphosphoryl azide and in the presence of a base such as triethylamine.

When A is —$NH_2$, —N═C═O or —N═C═S and B is —$NH_2$, or when A is —$NH_2$ and B is —N═C═O or —N═C═S the reaction is suitably carried out in an inert solvent for example dimethylformamide or dichloromethane and/or toluene at ambient or elevated temperature, preferably ambient.

When A is —$CON_3$ or —$CO_2H$ and B is —$NH_2$ the reaction is suitably carried out in an inert solvent for example toluene or dimethylformamide at elevated temperature.

Where A is —NHCOL and B is —$NH_2$ or when A is —$NH_2$ and B is —NHCOL, the reaction is suitably carried out in an inert solvent such as dichloromethane at ambient temperature optionally in the presence of a base, such as triethylamine or in dimethylformamide at ambient or elevated temperature.

When A is halogen and B is —$NHCONH_2$ the reaction is suitably carried out in an inert solvent such as toluene at elevated temperature, optionally in the presence of base.

Suitable examples of compounds having groups $R^{1'}$ to $R^{6'}$ which are convertible to $R^1$ to $R^6$ respectively include compounds where an adjacent pair of $R^{2'}$ to $R^{6'}$ together with the carbon atoms to which they are attached represent a fused pyrrole ring which is unsubstituted on nitrogen, where treatment with a base, e.g. sodium hydride, and reaction with an electrophile, e.g. methyl iodide, benzyl chloride or benzenesulfonyl chloride, affords the corresponding substituent on the pyrrole nitrogen.

Compounds of formula (II) where A is —$NH_2$ are known compounds or can be prepared analogously to known compounds.

Compounds of formula (II) where A is —N═C═O may be prepared by treating a compound of formula (II) in which:
(i) A is amino, with phosgene or a phosgene equivalent, in the presence of excess base or an inert solvent.
(ii) A is acylazide (i.e. —$CON_3$), via the nitrene, by thermal rearrangement using conventional conditions (ref. L. S. Trifonov et al, *Helv. Chim. Acta*, 1987, 70, 262).
(iii) A is —$CONH_2$, via the nitrene intermediate using conventional conditions.

Compounds of formula (II) where A is —N═C═S are known compounds or can be prepared analogously to known compounds.

Compounds of formula (II) where A is —NHCOL may be prepared by reacting a compound of formula (II) in which A is —$NH_2$ with phosgene or a phosgene equivalent, in an inert solvent, at low temperature, if necessary in the presence of a base such as triethylamine.

Compounds of formula (II) in which A is halogen are known compounds or can be prepared analogously to known compounds.

Compounds of formula (III) where B is —$NH_2$ are known compounds or can be prepared analogously to known compounds.

Compounds of formula (III) where B is —N═C═O may be prepared by treating a compound of formula (III) in which:
(i) B is amino, with phosgene or a phosgene equivalent, in the presence of excess base or an inert solvent.
(ii) B is acylazide (i.e. —$CON_3$), via the nitrene, by thermal rearrangement using conventional conditions (ref. L. S. Trifonov et al, *Helv. Chim. Acta*, 1987, 70, 262).
(iii) B is —$CONH_2$, via the nitrene intermediate using conventional conditions.

Compounds of formula (UT) where B is —N═C═S are known compounds or can be prepared analogously to known compounds.

Compounds of formula (III) where B is —NHCOL may be prepared by reacting a compound of formula (III) in which B is —$NH_2$ with phosgene or a phosgene equivalent, in an inert solvent, at low temperature, if necessary in the presence of a base such as triethylamine. Examples of phosgene equivalents include triphosgene, carbonyldiimidazole, phenyl chloroformate and phenyl chlorothioformate.

Compounds of formula (III) where B is —$NHCONH_2$ can be prepared from the corresponding precursor where B is —$NH_2$ by reaction with an isocyanate under conventional conditions.

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I) or pharmaceutically acceptable salts thereof.

Novel intermediates of formulae (II) and (III) are also part of this invention.

According to a further feature of the invention we provide a compound of formula (II):

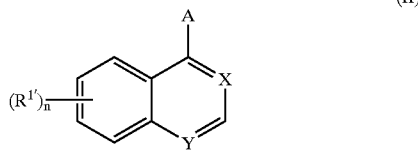

(II)

wherein A is —CON$_3$, —NH$_2$, —CO$_2$H, —N=C=O, —N=C=S, —NHCOL or halogen, L is a leaving group, X and Y are as defined in formula (I), n is 1, 2, 3 or 4, and R$^{1'}$ is R$^1$ as defined in formula (I) or a group convertible thereto.

Pharmaceutically acceptable salts may be prepared conventionally by reaction with the appropriate acid or acid derivative.

As indicated above the compounds of formula (I) and their pharmaceutically acceptable salts, including those compounds where X and Y both represent CH, and without provisos a)–f), are useful for the treatment of diseases or disorders where an antagonist of the human HFGAN72 receptor is required especially feeding disorders, such as obesity and diabetes; prolactinoma; hypoprolactinemia; hypothalamic disorders of growth hormone deficiency; idiopathic growth hormone deficiency; Cushings syndrome/disease; hypothalamic-adrenal dysfunction; dwarfism; sleep disorders; sleep apnea; narcolepsy; insomnia; parasomnia; jet-lag syndrome; and sleep disturbances associated with such diseases as neurological disorders, neuropathic pain, restless leg syndrome, heart and lung diseases, mental illness such as depression or schizophrenia, and addictions; sexual dysfunction; psychosexual dysfunction; sex disorder; sexual disorder; bulimia; and hypopituitarism.

The compounds of formula (I) and their pharmaceutically acceptable salts, including those compounds in which X and Y both represent CH, and without provisos a)–f), are particularly useful for the treatment of obesity, including obesity associated with Type 2 diabetes, and sleep disorders.

Other diseases or disorders which may be treated in accordance with the invention include disturbed biological and circadian rhythms; adrenohypophysis disease; hypophysis disease; hypophysis tumor/adenoma; adrenohypophysis hypofunction; functional or psychogenic amenorrhea; adrenohypophysis hyperfunction; migraine; hyperalgesia; pain; enhanced or exaggerated sensitivity to pain such as hyperalgesia, causalgia and allodynia; acute pain; burn pain; atypical facial pain; neuropathic pain; back pain; complex regional pain syndromes I and II; arthritic pain; sports injury pain; pain related to infection, e.g. HIV, post-polio syndrome and post-herpetic neuralgia; phantom limb pain; labour pain; cancer pain; post-chemotherapy pain; post-stroke pain; post-operative pain; neuralgia; and tolerance to narcotics or withdrawal from narcotics.

The present invention also provides a method of treating or preventing diseases or disorders where an antagonist of the human HFGAN72 receptor is required, which comprises administering to a subject in need thereof an effective amount of a compound of formula (I) or a pharmaceutically acceptable salt thereof, without the proviso that X and Y do not both represent CH and without provisos a)–f).

The present invention also provides a compound of formula (I) or a pharmaceutically acceptable salt thereof, without the proviso that X and Y do not both represent CH and without provisos a)–f), for use in the treatment or prophylaxis of disease or disorders where an antagonist of the human HFGAN72 receptor is required.

The present invention also provides the use of a compound of formula (I) or a pharmaceutically acceptable salt thereof, without the proviso that X and Y do not both represent CH and without provisos a)–f), in the manufacture of a medicament for the treatment or prophylaxis of diseases or disorders where an antagonist of the human HFGAN72 receptor is required.

For use in medicine, the compounds of the present invention are usually administered as a pharmaceutical composition. The present invention also provides a pharmaceutical composition comprising a compound of formula (I) or a pharmaceutically acceptable salt thereof and a pharmaceutically acceptable carrier.

The compounds of formula (I) and their pharmaceutically acceptable salts, including those compounds in which X and Y both represent CH and without provisos a)–f), may be administered by any convenient method, for example by oral, parenteral, buccal, sublingual, nasal, rectal or transdermal administration and the pharmaceutical compositions adapted accordingly.

The compounds of formula (I) and their pharmaceutically acceptable salts, including those compounds in which X and Y both represent CH and without provisos a)–f), which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon or hydrofluorocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

The dose of the compound of formula (I) or a pharmaceutically acceptable salt thereof, including those compounds in which X and Y both represent CH and without provisos a)–f), used in the treatment or prophylaxis of the abovementioned disorders or diseases will vary in the usual way with the particular disorder or disease being treated, the weight of the subject and other similar factors. However as a general rule suitable unit doses may be 0.05 to 1000 mg, more suitably 0.05 to 20.0 mg, for example 0.2 to 5 mg; such unit doses may be administered more than once a day for example two or three times a day, so that the total daily dosage is in the range of about 0.01 to 100 mg/kg; and such therapy may extend for a number of weeks or months. In the case of physiologically acceptable salts the above figures are calculated as the parent compound of formula (I), including those compounds in which X and Y both represent CH and without provisos a)–f).

No toxicological effects are indicated/expected when a compound of formula (I), including those compounds in which X and Y both represent CH and without provisos a)–f), is administered in the above mentioned dosage range.

The human HFGAN72 receptor ligand 72A referred to above has the amino acid sequence:

```
Gln Pro Leu Pro Asp Cys Cys Arg Gln Lys Thr Cys
1              5                       10

Ser Cys Arg Leu Tyr Glu Leu Leu His Gly Ala Gly Asn
His Ala Ala
            15              10 10 20

Asn His Ala Ala Gly Ile Leu Thr Leu-NH2
25                  30
```

The HFGAN72 receptor ligand referred to above can be employed in a process for screening for compounds (antagonists) which inhibit the ligand's activation of the HFGAN72 receptor.

In general, such screening procedures involve providing appropriate cells which express the HFGAN72 receptor on the surface thereof. Such cells include cells from mammals, yeast, Drosophila or E. coli. In particular, a polynucleotide encoding the HFGAN72 receptor is employed to transfect cells to thereby express the receptor. The expressed receptor is then contacted with a test compound and an HFGAN72 receptor ligand to observe inhibition of a functional response.

One such screening procedure involves the use of melanophores which are transfected to express the HFGAN72 receptor. Such a screening technique is described in WO 92/01810.

Another such screening technique involves introducing RNA encoding the HFGAN72 receptor into Xenopus oocytes to transiently express the receptor. The receptor oocytes may then be contacted with a receptor ligand and a compound to be screened, followed by detection of inhibition of a signal in the case of screening for compounds which are thought to inhibit activation of the receptor by the ligand.

Another method involves screening for compounds which inhibit activation of the receptor by determining inhibition of binding of a labelled HFGAN72 receptor ligand to cells which have the receptor on the surface thereof. Such a method involves transfecting a eukaryotic cell with DNA encoding the HFGAN72 receptor such that the cell expresses the receptor on its surface and contacting the cell or cell membrane preparation with a compound in the presence of a labelled form of an HFGAN72 receptor ligand. The ligand can be labelled, e.g. by radioactivity. The amount of labelled ligand bound to the receptors is measured, e.g. by measuring radioactivity of the receptors. If the compound binds to the receptor as determined by a reduction of labelled ligand which binds to the receptors, the binding of labelled ligand to the receptor is inhibited.

Yet another screening technique involves the use of FLIPR equipment for high throughput screening of test compounds that inhibit mobilisation of intracellular calcium ions, or other ions, by affecting the interaction of an HFGAN72 receptor ligand with the HFGAN72 receptor. The ligand used in the screening method described below to determine the antagonist activity of compounds according to the invention is Lig 72A which has the amino acid sequence shown above.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention. The following Descriptions D1–D33 illustrate the preparation of intermediates to compounds of the present invention.

In the Examples $^1$H NMR's were measured at 250 MHz in $d_6$-DMSO unless otherwise stated. All hydrochloride salts unless otherwise stated were prepared by dissolving/suspending the free-base in methanol and treating with an excess of ethereal HCl (1M).

Descriptions

D1 Methyl quinoline-4-carboxylate

Thionyl chloride (4.5 ml) was added dropwise, under argon to a cooled, stirring slurry of 4-quinolinecarboxylic acid (5.32 g) in methanol (120 ml) maintaining an internal temperature of 0 to −5° C. Once addition was complete the reaction mixture was heated at reflux for 16 h. After cooling to ambient temperature the volatiles were removed at reduced pressure and the residue partitioned between saturated aqueous sodium bicarbonate and diethyl ether. The organic phase was washed with brine, dried ($Na_2SO_4$) and the solvent removed at reduced pressure to give the title compound as a pale yellow oil (4.82 g).

$^1$H NMR (CDCl$_3$) δ: 4.05 (3H, s), 7.66 (1H, m), 7.77 (1H, m), 7.91 (1H, d, J 4 Hz), 8.18 (1H, dd, J 1+9 Hz), 8.78 (1H, dd, J 1+9 Hz), 9.02 (1H, d, J 4 Hz).

m/z (API$^+$): 188 (MH$^+$).

Alternatively the title ester can be prepared, using standard chemistry, in 42% yield from 4-quinolinecarboxylic acid, methanol and c.H$_2$SO$_4$.

D2 Quinoline-4-carboxylic acid hydrazide

D1 (1.35 g) in ethanol (50 ml) was treated with hydrazine hydrate (2.0 ml, 98%, excess) and the mixture heated at reflux under argon for 14 h. The reaction mixture was cooled to ambient temperature and the volatiles removed at reduced pressure. Trituration of the residue with diethyl ether gave the title compound as a yellow solid (1.32 g).

¹H NMR δ: 4.46 (2H, bs), 7.33 (1H, d, J 4 Hz), 7.48 (1H, m), 7.63 (1H, m), 7.90 (1H, d, J 8 Hz), 7.99 (1H, d, J 8 Hz), 8.78 (1H, d, J 4 Hz), 9.75 (1H, bs).

m/z (API⁺): 188 (MH⁺).

D3 Quinoline-4-carbonyl azide

A cooled slurry of D2 (1.34 g) in water (5.00 ml) was treated drop-wise with c.HCl (1.44 ml) maintaining an internal temperature of 0 to 5° C. A cooled solution of sodium nitrite (1.08 g) in water (1.44 ml) was added dropwise over 15 min maintaining the same internal temperature. The solution was then neutralised with saturated aqueous sodium bicarbonate. The title compound was collected by filtration as a white solid which was washed with water then dried at reduced pressure at ambient temperature (1.00 g).

¹H NMR (CDCl₃) δ: 7.72 (1H, m), 7.82 (1H, m), 7.95 (1H, d, J 4 Hz), 8.19 (H, d, J 8 Hz), 8.91 (1H, d, J 8 Hz), 9.05 (1H, d, J 4 Hz).

D4 4-Aminoquinoline

Method 1

A mixture of 4-nitroquinoline-N-oxide (0.700 g) and 10% palladium on charcoal (0.700 g) was hydrogenated at atmospheric pressure for 16 h. The catalyst was removed by filtration and the methanol removed at reduced pressure. As ¹H NMR indicated that starting material still remained the hydrogenation was repeated with a further batch of catalyst (0.500 g) and worked up as described previously. The resulting residue was recrystallised (methanol/toluene/hexane) to give the title amine as a solid (0.350 g).

¹H NMR δ: 6.55 (1H, d, J 5 Hz), 6.77 (2H, s), 7.37 (1H, m), 7.60 (1H, m), 7.74 (1H, d, J 8 Hz), 8.15 (1H, d, J 8 Hz), 8.27 (1H, d, J 5 Hz).

Method 2 a) Quinolin-4-yl carbamic acid tert butyl ester

Quinoline-4-carboxylic acid (13.0 g) and diphenylphosporyl azide (16.2 ml) were combined in tert butanol (180 ml) containing triethylamine (11 ml). The mixture was boiled for 24 h. Solvent was removed at reduced pressure and the residue partitioned between water and ethyl acetate. The aqueous phase was extracted with ethyl acetate (×4). The combined organinc extracts were washed with saturated brine, dried and solvent removed at reduced pressure. The residue was dissolved in methanol/ethyl acetate filtered and the filtrate evaporated at reduced pressure. The residue was column chromatographed (silica gel, ethyl acetate eluant) to give the title compound (16.8 g).

¹H NMR δ: 1.54 (9H, s), 7.53–7.59 (1H, m), 7.71 –7.77 (1H, m), 7.92 (1H, d, J 5.2 Hz), 7.96 (1H, d, J 8.4 Hz), 8.37 (1H, d, J 8.4 Hz), 8.75 (1H, d, J 5.2 Hz), 9.82 (1H, s).

b) 4-Aminoquinoline

A solution of quinolin-4-yl carbamic acid tert butyl ester (16.8 g) in 5N HCl (200 ml) was boiled for 5 h. The reaction mixture was diluted with water made basic with sodium hydroxide and washed with dichloromethane. The aqueous phase was separated and evaporated to dryness at reduced pressure. The residue was dissolved in propan-1-ol, insoluble material separated by filtration and the filtrate evaporated to dryness. The residue was dissolved in dichloromethane/ethyl acetate, filtered to remove insoluble inorganic salts and solvent removed at reduced pressure to give 4-aminoquinoline (8.7 g).

D5 Synthesis of 5-nitro-1-substituted-(1H)-indoles

5-Nitroindole and potassium or caesium carbonate (1.5 eq.) were stirred together for 15 min. in dimethylformamide. The alkyl halide (1.1 eq.) was added and the reaction mixture stirred until tlc indicated disappearance of 5-nitroindole. The mixture was poured into water and the precipitated product separated by filtration.

| Product | Product name | Alkyl halide | Base | m/z (M + H) | Yield |
|---|---|---|---|---|---|
| D5(A) | 1-ethyl-5-nitro-(1H)-indole | bromoethane | K₂CO₃ | 191 | 84% |
| D5(B) | 5-nitro-1-(3-phenylpropyl)-(1H)-indole | 3-phenylpropyl bromide | K₂CO₃ | 281 | 82% |
| D5(C) | 1-benzyl-5-nitro-(1H)-indole | Benzyl bromide | Cs₂CO₃ | 253 | 87% |
| D5(D) | 4-(5-Nitroindol-1-yl)butyric acid ethyl ester | ethyl 4-bromobutyrate | Cs₂CO₃ | 277 | 86% |
| D5(E) | 4-(5-Nitroindol-1-yl)butyronitrile | 3-cyanopropyl bromide | Cs₂CO₃ | 230 | 100% |

D6 Synthesis of 5-amino-1-substituted-(1H)-indoles

The appropriate 5-nitro-1-substituted-(1H)-indole (1 g) and 10% palladium/charcoal (0.5 g) in ethanol (120 ml) was treated with ammonium formate (5 eq.) in one portion and the mixture stirred for 16 h. The mixture was filtered through a celite pad and solvent removed at reduced pressure. The residue was partitioned between water and ethyl acetate, washed with water and sodium bicarbonate to give, after drying (Na₂SO₄) and removal of solvent at reduced pressure, the required compound.

| Starting Material | Product | Product name | m/z (M+ H) | Yield |
|---|---|---|---|---|
| D5(A) | D6(A) | 5-amino-1-ethyl-(1H)-indole | 161 | 56% |
| D5(B) | D6(B) | 5-amino-1-(3-phenylpropyl)-(1H)-indole | 251 | 31% |
| D5(C) | D6(C) | 5-amino-1-benzyl-(1H)-indole | 223 | 100% |
| D5(D) | D6(D) | 4-(5-aminoindol-1-yl)butyric acid ethyl ester | 247 | 55% |
| D5(E) | D6(E) | 4-(5-aminoindol-1-yl)butyronitrile | 200 | 80% |

D7 Synthesis of 5-nitro-1-substituted-(1H)-indolines

5-Nitroindoline was dissolved in dimethylformamide (4 ml/mmol), sodium hydride added (1.5 eq., 60% suspension in oil) and the mixture stirred for 1 h. The appropriate alkylating agent (2 eq.) was added and the mixture stirred until tlc showed complete reaction. The mixture was poured into water and the precipitated product collected by filtration.

| Product | Product name | Alkyl Halide | Time | m/z (M + H) | Yield |
|---|---|---|---|---|---|
| D7(A) | 1-methyl-5-nitro-(1H)-indoline | iodomethane | 6 h | 179 | 83% |

D8 Synthesis of 5-amino-1-substituted-(1H)-indolines

The appropriate 5-nitro-1-substituted-(1H)-indoline was stirred in a mixture of methanol/water and sodium dithionite (4.5 eq.) and sodium hydrogen carbonate (4.5 eq.) added. The mixture was stirred at room temperature overnight and methanol removed at reduced pressure. The aqueous residue was extracted with ethyl acetate (2×). The combined organic phases were washed with water, dried ($Na_2SO_4$), and solvent removed at reduced pressure to give the target 5-amino-1-substituted-(1H)-indoline.

| Starting material | Product | Product Name | m/z (M + H) | Yield |
|---|---|---|---|---|
| D7(A) | D8(A) | 5-amino-1-methyl-1H-indoline | 149 | 56% |

D9 2-[(2-Bromo-5-methoxyphenylamino)methylene]malonic acid diethyl ester

A mixture of 3-amino-4-bromoanisole (1.40 g) and diethyl ethoxymethylene-malonate (1.4 ml) was heated at 100° C. for 4 h. The reaction mixture was cooled and ethanol removed at reduced pressure to give the title compound as a waxy brown solid (2.55 g).

$^1$H NMR ($CDCl_3$) δ: 1.34 (3H, t), 1.39 (3H, t), 3.83 (3H, s), 4.26 (2H, q), 4.35 (2H, q), 6.58 (1H, dd, J 2.7+8.8 Hz), 6.80 (1H, d, J 2.7 Hz), 7.46 (1H, d, J 8.8 Hz), 8.46 (1H, d, J 13 Hz), 11.20 (1H, d, J 13 Hz).

D10 8-Bromo-4-chloro-5-methoxyquinoline-3-carboxylic acid ethyl ester

D9 (2.55 g) in phosphoryl chloride (10 ml) was boiled for 16 h. Excess phosphoryl chloride was removed at reduced pressure, the residue dissolved in dichloromethane and washed with aqueous sodium hydrogen carbonate. The organic phase was dried ($Na_2SO_4$), solvent removed at reduced pressure and the residue triturated with hexane/diethyl ether to give the title compound (2.05 g) as a beige solid.

$^1$H NMR ($CDCl_3$) δ: 1.44 (3H, t), 3.99 (3H, s), 4.49 (2H, q), 6.89 (1H, d), 8.04 (1H, d), 9.06 (1H, s).

D11 8-Bromo-4-(4-methoxybenzyl)amino-5-methoxyquinoline-3-carboxylic acid ethyl ester A mixture of D10 (2.1 g) and 4-methoxybenzylamine (1.57 ml) in xylene (40 ml) was boiled for 4 h. The mixture was cooled to room temperature, filtered and the residue washed with xylene. The combined filtrate and washings were washed with sodium bicarbonate and brine, dried ($Na_2SO_4$) and solvent removed at reduced pressure to give after chromatography (silica gel, ethyl acetate/hexane 20%–50%) the title compound (2.13 g) as a waxy yellow solid.

$^1$H NMR ($CDCl_3$) δ: 1.40 (3H, t), 3.81 (3H, s), 3.84 (3H, s), 4.21 (2H, d), 4.40 (2H, q), 6.67 (1H, d), 6.87 (2H, d), 7.21 (2H, d), 7.86 (1H, d), 8.64 (1H, bs), 9.00 (1H, s).

D12 4-(4-Methoxybenzyl)amino-5-methoxyquinoline-3-carboxylic acid ethyl ester A slurry of palladium on charcoal (10%, 0.5 g) in ethanol (8 ml) was added to D11 (2.0 g) in ethanol (90 ml). Ammonium formate (1.88 g) was added and the mixture stirred at room temperature for 6 h, filtered and solvent removed at reduced pressure. The residue was dissolved in ethyl acetate, washed with aqueous sodium bicarbonate and brine, dried ($Na_2SO_4$) and solvent removed at reduced pressure to give the title compound (1.50 g) as a yellow gum.

$^1$H NMR ($CDCl_3$) δ: 1.41 (3H, t), 3.81 (3H, s), 3.84 (3H, s), 4.21 (2H, d), 4.40 (2H, q), 6.79 (1H, dd), 6.89 (2H, d), 7.22 (2H, d), 7.48–7.59 (2H, m), 8.59 (1H, bs), 8.87 (1H, s).

D13 4-(4-Methoxybenzyl)amino-5-methoxyquinoline-3-carboxylic acid

D12 (1.50 g) was added to a solution of potassium hydroxide (0.35 g) in aqueous ethanol (55 ml, 10:1) and the mixture boiled for 16 h. Additional potassium hydroxide (0.1 g) was added and heating continued for a further 6 h. Ethanol was removed at reduced pressure. The residue was treated with water (75 ml) and washed with ethyl acetate. The aqueous phase was acidified with 5N HCl, sodium hydrogen carbonate added and finally acetic acid. The gel generated was separated by filtration and the residue dried in vacuo to give the title compound (1.42 g) as a brown solid.

m/z ($API^+$): 295 ($MH^+$).

D14 4-(4-Methoxybenzyl)amino-5-methoxyquinoline

D13 (1.42 g) was boiled in diphenyl ether (10 ml) for 15 min. The cooled solution was poured into hexane with vigorous stirring and the precipitated product collected by filtration to give the title compound (1.15 g).

$^1$H NMR ($CDCl_3$) δ: 3.82 (3H; s), 3.94 (3H, s), 4.41 (2H, d), 6.29 (1H, d), 6.74 (1H, d), 6.91 (2H, d), 7.30 (2H, d), 7.47 (1H, t), 7.57 (1H, d), 7.97 (1H, bs), 8.39 (1H, d).

D15 4-Amino-5-methoxyquinoline

D14 (1.14 g) was cooled (ice bath) and trifluoroacetic acid (10 ml) added, followed by anisole (0.81 ml) and c.$H_2SO_4$ (1 drop). The mixture was stirred at room temperature for 4 h, poured onto ice and neutralised with potassium carbonate. The aqueous phase was extracted with dichloromethane (4×30 ml), the combined organic extracts washed with water, dried ($Na_2SO_4$) and solvent removed at reduced pressure. The residue was column chromatographed to give the title compound (0.25 g) as a pale brown solid.

$^1$H NMR ($CDCl_3$) δ: 3.98 (3H, s), 5.95 (2H, bs), 6.39 (1H, d), 6.71 (1H, dd), 7.43–7.56 (2H, m), 8.36 (1H, d).

D16 8-Bromoquinoline-4-carboxylic acid hydrazide

The title compound (0.95 g) as a yellow solid was obtained according to the method of D2 from 8-bromoquinolin-4-carboxylic acid ethyl ester (1.04 g, E. R. Buchman et al., *J. Amer. Chem. Soc.*, 1946, 68, 2692) in ethanol (40 ml) and hydrazine hydrate (1.2 ml, 98%), the mixture was boiled for 6 h, additional hydrazine hydrate (0.5 ml) added and heating continued for a further 16 h.

m/z ($API^+$): 267 ($MH^+$).

D17 8-Bromoquinoline-4-carboxylic acid azide

From D16 (0.92 g) in water (8 ml), c.HCl (0.72 ml) and sodium nitrite (0.52 g) in water (0.8 ml), the title compound (0.85 g) was obtained according to the method of D3.

$^1$H NMR δ: 7.69 (1H, t), 8.07 (1H, d), 8.29 (1H, d), 8.76 (1H, d), 9.21 (1H, d).

D18 2-(2-Methoxyphenylamino)methylenemalonic acid diethyl ester

From 2-anisidine (12.3 g) and diethyl ethoxymethylenemalonate (21.6 g) the title compound (29 g) was obtained as a waxy brown solid according to the method of D9.

$^1$H NMR (CDCl$_3$) δ: 1.33 (3H, t), 1.37 (3H, t), 3.93 (3H, s), 4.24 (2H, q), 4.33 (2H, q), 6.90–7.01 (2H, m), 7.09 (1H, t), 7.24 (1H, d), 8.56 (1H, d), 11.08 (1H, d).

D19 4-Chloro-8-methoxyquinoline-3-carboxylic acid ethyl ester

D18 (10 g) in phosphoryl chloride (15 ml) was boiled for 2 h. Excess phosphoryl chloride was removed at reduced pressure and the residue azeotroped with toluene (2×50 ml). The residue was dissolved in ethyl acetate, washed with aqueous sodium hydrogen carbonate, the organic phase dried (Na$_2$SO$_4$) and solvent removed at reduced pressure to give the title compound (7.96 g) as a brown oil.

$^1$H NMR (CDCl$_3$) δ: 1.47 (3H, t), 4.11 (3H, s), 4.49 (2H, q), 7.20 (1H, d), 7.63 (1H, t), 7.97 (1H, d), 9.18 (1H, s).

D20 4-(4-Methoxybenzyl)amino-8-methoxyquinoline-3-carboxylic acid ethyl ester From D19 (11.97 g), 4-methoxybenzylamine (11.8 ml) in xylene (100 ml), boiling for 12 h and washing with dichloromethane, the title compound (15.0 g) was obtained as a waxy yellow solid according to the method of D11.

m/z (API$^+$): 367 (MH$^+$).

D21 4-(4-Methoxybenzyl)amino-8-methoxyquinoline-3-carboxylic acid

D20 (14.68 g) was boiled in a mixture of 2N sodium hydroxide and ethanol (250 ml, 2:3) for 2 h. The reaction mixture was cooled and acetic acid (15 ml) added. Ethanol (100 ml) was removed and the precipitated title compound collected by filtration.

m/z (API$^+$): 339 (MH$^+$).

D22 4-(4-Methoxybenzyl)amino-8-methoxyquinoline

From D21 (1.0 g) and diphenyl ether (5 ml) the title compound (0.78 g) was obtained as a brown solid according to the method of D14.

m/z (API$^+$): 295 (MH$^+$).

D23 4-Amino-8-methoxyquinoline

From D22 (0.73 g) and anisole (0.52 ml) the title compound (0.40 g) was obtained as a pale brown solid according to the method of D15.

$^1$H NMR (CDCl$_3$) δ: 4.06 (3H, s), 4.69 (2H, bs), 6.63 (1H, d), 7.01 (1H, d), 7.29–7.41 (2H, m), 8.55 (1H, d).

D24 7-Bromoquinoline-4-carboxylic acid hydrazide

The title compound (0.295 g) was obtained as an off-white solid after trituration with diethyl ether from 7-bromoquinoline-4-carboxylic acid methyl ester (0.50 g) and hydrazine hydrate (0.6 ml) according to the method of D2.

m/z (API$^+$): 266, 268 (MH$^+$).

D25 7-Bromoquinoline-4-carboxylic acid azide

From D24 (0.254 g) in water (5 ml), c.HCl (0.20 ml) and sodium nitrite (0.143 g) in water (1.0 ml), the title compound (0.229 g) was obtained according to the method of D3.

$^1$H NMR δ: 7.96 (1H, dd), 8.03 (1H, d), 8.39 (1H, dd), 8.72 (1H, d), 9.14 (1H, d).

D26 6-Bromoquinoline-4-carboxylic acid hydrazide

The title compound (0.437 g) was obtained as an off-white solid after trituration with diethyl ether from 6-bromoquinoline-4-carboxylic acid ethyl ester (0.50 g) and hydrazine hydrate (0.6 ml) according to the method of D2.

m/z (API$^+$): 266, 268 (MH$^+$).

D27 6-Bromoquinoline-4-carboxylic acid azide

From D26 (0.405 g) in water (5 ml), c.HCl (0.30 ml) and sodium nitrite (0.228 g) in water (1.0 ml), the title compound (0.375 g) was obtained according to the method of D3 as a cream solid.

$^1$H NMR δ: 7.92–8.12 (3H, m), 8.99 (1H, d), 9.14 (1H, d).

D28 8-Acetyl-4-quinoline carboxylic acid methyl ester

8-Bromo4-quinoline carboxylic acid methyl ester, D16 (E. R. Buchman et al., *J. Amer. Chem. Soc.*, 1946, 68, 2692), (0.712 g), (1-ethoxyvinyl)tributyltin (1.60 g) and tetrakis (triphenylphosphine)palladium (O) in 1,4-dioxane (50 ml) were heated at reflux for 16 h. The reaction mixture was cooled to ambient temperature, HCl (5M, 1 ml) and water (15 ml) added and the resulting mixture stirred for 3 h. The solvent was removed at reduced pressure, the residue suspended in EtOAc and the solid removed by filtration. The organic phase was washed with saturated sodium bicarbonate, dried (Na$_2$SO$_4$), removal of the solvent under reduced pressure gave a dark oil which was chromatographed (silica gel, hexane diethyl ether) to give the title compound (0.500 g).

$^1$H NMR (CDCl$_3$) δ: 2.90 (3H, s), 4.06 (3H, s), 7.70 (1H, dd, J 8+9 Hz), 7.94 (2H, m), 8.90 (1H, dd, J 1+9 Hz), 9.07 (1H, d, J 4 Hz).

m/z (API$^+$): 230 (MH$^+$).

D29 8-Acetyl-4-quinolinecarboxylic acid

D28 (0.490 g) in methanol (5 ml) was stirred with NaOH (2M, 3 ml) under argon for 2.5 h. After addition of c.HCl to pH1, solvent was removed at reduced pressure. The residue was triturated with ethanol and propan-1-ol, the mixture filtered to remove the in organics and the solvent removed under reduced pressure to give the title compound as a pale orange solid (0.360 g).

$^1$H NMR δ: 2.78 (3H, s), 7.81 (1H, dd, J 8 Hz), 7.93 (1H, d, J 8 Hz), 8.03 (1H, d, J 4 Hz), 8.09 (1H, d, J 8 Hz), 9.14 (1H, d, J 4 Hz).

D30 Benzoxazole-6-carboxylic acid

4-Amino-3-hydroxybenzoic acid (2.200 g) and formic acid (20 ml) were heated at 117° C. for 4 h. The reaction mixture was cooled to ambient temperature and the precipitated solid collected by filtration, washed with diethyl ether and dried at reduced pressure. The solid (0.580 g) was heated at reflux with zinc chloride (2.00 g) and c.H$_2$SO$_4$ (2 drops) in xylene (150 ml) under a Dean and Stark for 16 h. On cooling, water was added and the brown solid collected by filtration and washed with water. The resulting solid was washed with methanol and the solvent removed from the filtrate under reduced pressure to give the title compound as a dark brown solid (0.349 g).

$^1$H NMR δ: 7.90 (1H, d, J 8 Hz), 8.02 (1H, dd, J 1+8 Hz), 8.29 (1H, d, J 2 Hz), 8.94 (1H, s).

D31 Benzoxazole-5-carboxylic acid

From 3-amino-2-hydroxybenzoic acid (1.049 g) the title compound (0.800 g) was prepared according to the method of D30.

$^1$H NMR δ: 7.89 (1H, d, J 8 Hz), 8.07 (1H, dd, J 2+8 Hz), 8.33 (1H, d, J 2 Hz), 8.89 (1H, s).

D32 6-Fluoroquinoline-2,4-dicarboxylic acid

5-Fluoroisatin (9.74 g) was added to a hot solution of 33% potassium hydroxide (29.1 g in 85 ml water). Pyruvic acid (9.25 g) was added, the mixture stirred at room temperature for 1 h and boiled for 1 h. The mixture was cooled to room temperature and acidified with c.HCl. After refridgerating overnight, the precipitated material was collected by filtration and dried in vacuo at 50° C. to give the title compound (14.5 g).

$^1$H NMR δ: 7.85–7.93 (1H, m), (1H, dd, J 5.9+9.3 Hz), 8.59 (1H, dd, J 5.7+9.3 Hz), 13.90 (2H, bs).

m/z (API$^+$): 236 (MH$^+$).

D33 6-Fluoroquinoline-4-carboxylic acid

6-Fluoroquinoline-2,4-dicarboxylic acid (14.2 g) in nitrobenzene (50 ml) was boiled for 30 min in a reaction vessel equipped with a Dean-Stark apparatus. The mixture was cooled to room temperature and the precipitated material triturated with 60–80 petroleum ether (500 ml). The solid precipitated title compound (10.50 g) was collected by filtration and dried in vacuao.

$^1$H NMR δ: 7.79 (1H, dt, J 2.9+9.2 Hz), 8.04 (1H, d, J 4.4 Hz), 8.21 (1H, dd, J 5.7+9.3 Hz), 8.52 (1H, dd, J 2.9+11.2 Hz), 9.05 (1H, d, J 4.4 Hz).

m/z (API$^+$): 192 (MH$^+$).

EXAMPLES

1. 1-(1-Methyl-1H-indol-5-yl)-3-quinolin-4-ylurea and 1-(1-methyl-1H-indol-5-yl)-3-quinolin4-yl)urea hydrochloride Method 1

D3 (1.00 g) in dry toluene (20 ml) was heated slowly to reflux and this temperature maintained for 1 h. The reaction mixture was cooled to ambient temperature, 5-amino-1-methylindole (WO93/18028) (0.73 g) in dichloromethane (30 ml) added and the mixture stirred under argon at ambient temperature for 16 h. The resulting precipitate was collected by filtration and washed with diethyl ether. Chromatography on silica gel eluting with 50–100% ethyl acetate in hexane gave the title compound as a pale pink solid (0.50 g).

$^1$H NMR δ: 3.78 (3H, s), 6.39 (1H, d, J 2 Hz), 7.21 (1H, dd, J 2 Hz), 7.31 (1H, d, J 2 Hz), 7.40 (1H, d, J 9 Hz), 7.67 (1H, m), 7.78 (2H, m), 7.98 (1H, d, J 9 Hz), 8.26 (2H, m), 8.72 (1H, d, J2 Hz), 9.15 (1H, s), 9.18 (1H, s).

m/z (API$^+$): 317 (MH$^+$).

The hydrochloride salt of the title compound was prepared as a yellow solid.

m/z (API$^+$): 317 (MH$^+$).

Method 2

D4 (0.211 g) and carbonyldiimidazole (0.260 g) were stirred in dichloromethane (4 ml) under argon at ambient temperature for 0.5 h. The solvent was removed at reduced pressure and 5-amino-1-methylindole (0.214 g) and dimethylformamide (10 ml) added. The mixture was heated at 90° C. for 0.5 h under argon with stirring. The cooled mixture was treated dropwise with water and the precipitated solid collected by filtration. Chromatography on silica gel eluting with dichloromethane followed by recrystallisation from ethanol gave the title compound (0.065 g).

Method 3

A mixture of 4-quinolinecarboxylic acid (0.168 g), triethylamine (0.13 ml) and diphenylphosphoryl azide (0.21 ml) in dimethylformamide (5 ml) was heated under argon at 63° C. for 0.5 h. The reaction was cooled to ambient temperature and 1-methyl-5-aminoindole (0.130 g) added. The mixture was heated for a further 16 h then allowed to cool. The resulting solution was partitioned between dichloromethane and water, the organic phase was dried (Na$_2$SO$_4$) and the solvent removed at reduced pressure. The residue was chromatographed on silica gel eluting with 20% ethyl acetate in hexane-acetone to give the title compound as a pale pink solid (0.015 g).

2. 1-(1-Ethyl-1H-indol-5-yl)-3-quinolin-4-ylurea

From D3 (0.22 g) and 5-amino-1-ethyl-(1H)-indole D6(A) (0.18 g) the title compound (0.03 g), after recrystallisation from ethanol, was prepared according to Example 1, Method 1.

$^1$H NMR δ: 1.36 (3H, t, J 7 Hz), 4.20 (2H, q, J 7 Hz), 6.41 (1H, d, J 3 Hz), 7.25 (1H, dd), 7.39 (1H, d, J 3 Hz), 7.46 (1H, d, J 9 Hz), 7.83 (2H, m), 7.98 (1H, t, J 8 Hz), 8.07 (1H, d, J 8 Hz), 8.57 (1H, d, J 6 Hz), 8.76 (1H, d, J 8 Hz), 8.87 (1H, d, J 6 Hz), 10.13 (1H, s), 10.24 (1H, bs).

m/z (API$^+$): 331 (MH$^+$).

3. 1-[1-(3-Phenylpropyl)-1H-indol-5-yl]-3-quinolin-4-ylurea

From D3 (0.22 g) and 5-amino-1-(3-phenylpropyl)-(1H)-indole D6(B) (0.28 g) the title compound (0.14 g), after trituration with diethyl ether, was prepared according to Example 1, Method 1.

$^1$H NMR δ: 2.08 (2H, m), 2.57 (2H, t), 4.19 (2H, t), 6.41 (1H, d), 7.18–7.32 (6H), 7.38–7.42 (2H, m), 7.64–7.80 (3H, m) 7.97 (1H, d), 8.23–8.28 (2H, m), 8.71 (1H, d), 9.21 (2H, bs).

m/z (API$^+$): 421 (MH$^+$).

4. 1-(1-Benzyl-1H-indol-5-yl)-3quinolin-4-ylurea

From D4 (0.245 g) and 5-amino-1-benzyl-(1H)-indole D6(C) (0.37 g) the title compound (0.25 g), after column chromatography (silica gel, hexane→ethyl acetate) and trituration with diethyl ether, was prepared according to Example 1, Method 2.

$^1$H NMR δ: 5.41 (2H, s), 7.11–7.42 (8H, m), 7.51 (1H, d), 7.64–7.82 (3H, m), 7.98 (1H, d), 8.21 –8.27 (2H, m), 8.71 (1H, d), 9.14 (1H, bs), 9.23 (1H, bs).

m/z (API$^+$): 393 (MH$^+$).

5. 1-[1-(3-Carboethoxypropyl)-1H-indol-5-yl]-3-quinolin-4-ylurea

From D3 (0.22 g) and 4-(5-aminoindol-1-yl)butyric acid ethyl ester D6(D), (0.27 g) the title compound (0.29 g) was prepared according to Example 1, Method 1.

¹H NMR δ: 1.34 (3H, t), 2.12–2.24 (2H, m), 2.44 (2H, t), 4.21 (2H, q), 4.37 (2H, t), 6.59 (1H, d), 7.38 (1H, dd), 7.52 (1H, d), 7.63 (1H, d), 7.82–7.98 (3H, m), 8.15 (1H, d), 8.42–8.46 (2H, m), 8.89 (1H, d), 9.40 (2H, bs).

m/z (API⁺): 417 (MH⁺).

6. 1-[1-(3-Cyanopropyl)-1H-indol-5-yl]-3-quinolin-4-ylurea hydrochloride

From D3 (0.22 g) and 4-(5-aminoindol-1-yl)butyronitrile D6(E), (0.27 g) the title compound (0.29 g) was prepared according to Example 1, Method 1.

¹H NMR δ: 2.09 (2H, t), 2.47 (2H, t), 4.25 (2H, t), 6.46 (1H, d, J 3 Hz), 7.29 (1H, dd, J9+2 Hz), 7.40 (1H, d), 7.50 (1H, d), 7.86–7.94 (2H, m), 8.07–8.18 (2H, m), 8.77 (1H, d), 8.97 (1H, d), 9.16 (1H, d), 10.89 (1H, s), 11.12 (1H, s).

m/z (API⁺): 370 (MH⁺).

7. 1-(1H-Indol-5-yl)-3quinolin-4-ylurea

From D3 (2.64 g) and 5-amino-(1H)-indole (1.77 g) the title compound (2.96 g) was prepared according to Example 1, Method 1.

¹H NMR δ: 6.30 (1H, d), 7.05 (1H, dd), 7.23–7.29 (2H, m), 7.55–7.69 (3H, 7.88 (1H, d), 8.13–8.18 (2H, m), 8.61 (1H, d), 9.06 (2H, bs), 10.93 (1H, bs).

m/z (API⁺): 303 (MH⁺).

8. 1-(1-Methyl-1H-indolin-5-yl)-3-quinolin-4-ylurea and 1-(1-methyl-1H-indolin-5-yl)-3-quinolin-4-ylurea dihydrochloride From D3 (0.203 g) and 5-amino-1-methyl-(1H)-indoline D8(A) (0.150 g) the title free base was prepared according to Example 1, Method 1 (0.290 g). Free base ¹H NMR δ: 2.67 (3H, s), 2.87 (2H, t, J 8 Hz), 3.21 (2H, t, J 8 Hz), 6.49 (1H, d, J 8 Hz), 7.11 (1H, dd, J2+8 Hz), 7.27 (1H, s), 7.65 (1H, t), 7.76 (1H, t), 7.97 (1H, d), 8.22 (2H, m), 8.69 (1H, d), 9.11 (2H, bs).

m/z (API⁺): 319 (MH⁺).

9. 1-(2,3-Dihydrobenzo[1,4]dioxin-6-yl)-3-quinolin-4-ylurea hydrochloride

From D3 (0.085 g) and 6-amino-1,4-benzodioxan (0.076 g) the title compound (0.08 g) was prepared according to Example 1, Method 1.

¹H NMR δ: 4.22–4.25 (4H, m), 6.85 (1H, d, J 9 Hz), 6.93 (1H, dd, J 2+9 Hz), 7.20 (1H, d, J 2 Hz), 7.91 (1H, t), 8.07–8.17 (2H, m), 8.71 (1H, d, J 7 Hz), 8.98 (1H, d, J 7 Hz), 9.07 (1H, d, J 9 Hz), 10.84(1H, s), 11.01 (1H, s).

m/z (API⁺): 322 (MH⁺).

10. 1-Benzo[1,3]dioxol-5-yl-3-quinolin-4-ylurea hydrochloride

From D3 (0.085 g) and benzo[1,3]dioxol-5-yl-ylamine (0.071 g) the title compound (0.12 g), was prepared according to Example 1, Method 1.

¹H NMR δ: 6.02 (2H, s), 6.91 (2H, s), 7.29 (1H, s), 7.88–7.94 (1H, m), 8.07–8.18 (2H, m), 8.70 (1H, d, J 7 Hz), 8.98 (1H, d, J 7 Hz), 9.09 (1H, d, J 9 Hz), 10.96 (1H, s), 11.04 (1H, s).

m/z (API⁺): 308 (MH⁺).

11. 1-(4-Methoxyphenyl)-3-quinolin-4-ylurea

A solution of D4 (0.083 g) in dimethylformamide (0.5 ml) was treated with 4-methoxyphenyl isocyanate (0.085 g). The reaction mixture was stirred for 16 h at ambient temperature, the solvent removed at reduced pressure and the residue was chromatographed on silica gel eluting with 50–100% ethyl acetate in hexane to give the title compound (0.023 g).

¹H NMR δ: 3.73 (3H, s), 6.93 (2H, d, J 9 Hz), 7.45 (2H, d, J 9 Hz), 7.68 (1H, m), 7.78 (1H, m), 7.99 (1H, d, J 8 Hz), 8.20 (2H, m), 8.7 (1H, d, J 5 Hz), 9.15 (1H, s), 9.20 (1H, s).

m/z (API⁺): 294 (MH⁺).

12. 1-(3-Methylthiophenyl)-3-quinolin-4-ylurea Hydrochloride

A solution of 3-methylthiophenyl isocyanate (0.165 g) in toluene (4 ml) was added to a stirred suspension of D4 (0.144 g) in dichloromethane (8 ml). The mixture was stirred for 48 h, diethyl ether (5 ml) added and the precipitated solid collected by filtration. The solid was washed with diethyl ether and hexane, suspended in methanol then treated with ethereal HCl (1M) to give the title compound (0.22 g) as a yellow solid.

¹H NMR δ: 2.49 (3H, s), 6.98–7.01 (1H, m), 7.27–7.36 (2H, m), 7.57 (1H, s), 7.92 (1H, t), 8.80–8.18 (2H, m), 8.71 (1H, d), 8.99 (1H, d), 9.06 (1H, d), 11.01 (2H, bs).

m/z (API⁺): 310 (MH⁺).

13. 1-(3,4-Dimethoxyphenyl)-3-quinolin-4-ylurea

D4 (0.124 g) and 3,4-dimethoxyphenyl isocyanate (Rasmussen et al, *J. Med. Chem.*, 1972, 21, 1044) (0.157 g) in dichloromethane (6 ml) was treated with 4-dimethylaminopyridine (0.005 g) in toluene (10 ml). The mixture was stirred for 16 h, solvent removed at reduced pressure and the residue triturated with dichloromethane/ diethyl ether (1:1) The resulting yellow solid was collected by filtration to give the title compound (0.094 g).

¹H NMR δ: 3.73 (3H, s), 3.78 (3H, s), 6.90–6.99 (2H, m), 7.24 (1H, d, J 1.67 Hz), 7.67 (1H, t), 7.77 (1H, t), 7.97 (1H, d), 8.19–8.24 (2H, m), 8.71 (1H, d, J 5.1 Hz), 9.20 (2H, s).

m/z (API⁺): 324 (MH⁺).

14. 1-(4-Methylthiophenyl)-3-quinolin-4-ylurea hydrochloride

D4 (0.20 g) and 4-methylthiophenyl isocyanate (0.23 g) in toluene/dichloromethane (18 ml, 10:8) containing 4-dimethylaminopyridine (0.002 g) was stirred at room temperature for 16 h. The precipitated solid was separated by filtration, suspended in methanol and excess ethereal HCl (1M) added. The title compound (0.313 g) isolated as a yellow solid was separated by filtration.

¹H NMR δ: 2.47 (3H, s), 7.30 (2H, d), 7.54 (2H, d), 7.91 (1H, dt), 8.08–8.18 (2H, m), 8.72 (1H, d), 9.01 (1H, d), 9.06 (1H, d), 10.95 (1H, s), 11.04 (1H, s).

m/z (API⁺): 310 (MH⁺).

15. 1-(3-Ethylphenyl)-3-quinolin-4-ylurea

A mixture of D4 (0.072 g) and 3-ethylphenyl isocyanate (0.088 g) in toluene/dichloromethane (7 ml, 4:3) containing 4-dimethylaminopyridine (0.002 g) was stirred at room temperature for 16 h. The precipitated solid was separated by filtration, washed with diethyl ether and dried to give the title compound (0.032 g).

¹H NMR δ: 1.28 (3H, t), 2.70 (2H, q), 6.98 (1H, d), 7.33 (1H, t), 7.41 (1H, m), 7.48 (1H, m), 7.76 (1H, t), 7.86 (1H, t), 8.07 (1H, d), 8.28–8.33 (2H, m), 8.81 (1H, d), 9.34 (2H, bd).

m/z (API⁺): 292 (MH⁺).

16. 1-(4-Ethoxyphenyl)-3-quinolin-4-ylurea

From 4ethoxyphenyl isocyanate (0.098 g) and D4 (0.072 g) the title compound (0.099 g) was prepared according to the method of Example 15.

$^1$H NMR δ: 1.22 (3H, t), 3.90 (2H, q), 6.82 (2H, d), 7.32 (2H, d), 7.57 (1H, t), 7.68 (1H, t), 7.88 (1H, d), 8.10–8.14 (2H, m), 8.62 (1H, d), 9.04 (1H, s), 9.09 (1H, s).

m/z (API$^+$): 308 (MH$^+$).

17. 1-(4-N,N-Dimethylaminophenyl)-3-quinolin-4-ylunea and 1-(4-N,N-Dimethylaminophenyl)-3-quinolin-4-ylurea dihydrochloride From 4-dimethylaminophenyl isocyanate (0.097 g) and D4 (0.072 g) the title compound (0.097 g) was prepared according to the method of Example 15.

$^1$H NMR δ: 2.78 (6H, s), 6.66 (2H, d), 7.26 (2H, d), 7.61 (1H, t), 7.68 (1H, t), 7.90 (1H, d), 8.11–8.16 (2H, m) 8.62 (1H, d), 8.92 (1H, bs), 9.06 (1H, bs).

m/z (API$^+$): 307 (MH$^+$).

The dihydrochloride was prepared.

$^1$H NMR δ: 3.06 (6H, s), 7.42 (2H, bs), 7.61 (2H, d), 7.93 (1H, t), 8.09–8.20 (2H, m), 8.74 (1H, d), 9.00 (1H, d), 9.15 (1H, d), 11.18 (2H, bs).

18. 1-(4-Carboethoxyphenyl)-3-quinolin-4-ylurea

From 4-carboethoxyphenyl isocyanate (0.096 g) and D4 (0.072 g) the title compound (0.095 g) was prepared according to the method of Example 15.

$^1$H NMR δ: 1.33 (3H, t), 4.30 (2H, q), 7.68 (2H, d), 7.71–7.84 (2H, m), 7.95–8.02 (3H, m), 8.19–8.29 (2H, m), 8.75 (1H, d), 9.35 (1H, s), 9.76 (1H, s).

m/z (API$^+$): 336 (MH$^+$).

19. 1-(4-n-Butylphenyl)-3-quinolin-4ylurea

From 4-n-butylphenyl isocyanate (0.088 g) and D4 (0.072 g) the title compound (0.020 g) was prepared according to the method of Example 15.

$^1$H NMR δ: 0.90 (3H, t), 1.31 (2H, m), 1.55 (2H, m), 2.50 (2H, m), 7.16 (2H, d), 7.42 (2H, d), 7.64–7.80 (2H, m), 7.99 (1H, d), 8.20–8.27 (2H, m), 8.72 (1H, d), 9.25 (2H, s).

m/z (API$^+$): 320 (MH$^+$).

20. 1-(4-Ethylphenyl)-3-quinolin-4-ylurea

From 4-ethylphenyl isocyanate (0.062 g) and D4 (0.072 g) the title compound (0.014 g) was prepared according to the method of Example 15.

$^1$H NMR δ: 1.06 (3H, t), 2.45 (2H, q), 7.07 (2H, d), 7.31 (2H, d), 7.56 (1H, t), 7.66 (1H, t), 7.87 (1H, d), 8.08–8.13 (2H, m), 8.60 (1H, d), 9.11 (2H, bd).

m/z (API$^+$): 292 (MH$^+$).

21. 1-(4-Trifluoromethoxyphenyl)-3-quinolin-4-ylurea

From 4-trifluoromethylphenyl isocyanate (0.122 g) and D4 (0.072 g) the title compound (0.025 g) was prepared according to the method of Example 15.

$^1$H NMR δ: 7.42 (2H, d), 7.71 (2H, d), 7.73 (1H, t), 7.85 (1H, t), 8.06 (1H, d), 8.26–8.29 (2H, m), 8.81 (1H, d), 9.48 (2H, bd).

m/z (API$^+$): 348 (MH$^+$).

22. 1-(4-Chlorophenyl)-3-quinolin-4-ylurea

From 4-chlorophenyl isocyanate (0.092 g) and D4 (0.072 g) the title compound (0.10 g) was prepared according to the method of Example 15.

$^1$H NMR δ: 7.47 (2H, d), 7.64 (2H, d), 7.76 (1H, t), 7.86 (1H, t), 8.07 (1H, d), 8.26–8.30 (2H, m), 8.81 (1H, d), 9.32 (1H, s), 9.51 (1H, s).

m/z (API$^+$): 298, 300 (MH$^+$).

23. 1-(3-Chlorophenyl)-3-quinolin-4-ylurea

From 3-chlorophenyl isocyanate (0.092 g) and D4 (0.072 g) the title compound (0.093 g) was prepared according to the method of Example 15.

$^1$H NMR δ: 6.92 (1H, m), 7.12–7.24 (2H, m), 7.49–7.65 (3H, m), 7.83 (1H, d), 8.02–8.06 (2H, m), 8.58 (1H, d), 9.15 (1H, bs), 9.33 (1H, bs).

m/z (API$^+$): 298, 300 (MH$^+$).

24. 1-(3-Chloro-4-methylphenyl)-3-quinolin-4-ylurea

From 3-chloro-4-methylphenyl isocyanate (0.129 g) and D4 (0.072 g) the title compound (0.136 g) was prepared according to the method of Example 15.

$^1$H NMR δ: 2.27 (3H, s), 7.14–7.31 (2H, m), 7.66 (1H, t), 7.72–7.78 (2H, m), 7.98 (1H, d), 8.16–8.20 (2H, m), 8.72 (1H, d), 8.23 (1H, s), 9.35 (1H, s).

m/z (API$^+$): 312, 314 (MH$^+$).

25. 1-(3-Cyanophenyl)-3-quinolin-4-ylurea

From 3-cyanophenyl isocyanate (0.086 g) and D4 (0.072 g) the title compound (0.08 g) was prepared according to the method of Example 15.

$^1$H NMR δ: 7.46–7.62 (2H, m), 7.71–7.84 (3H, m), 8.01–8.09 (2H, m), 8.22–8.24 (2H, d), 8.78 (1H, d), 9.40 (1H, s), 9.65 (1H, s).

m/z (API$^+$): 289 (MH$^+$).

26. 1-(3,4-Dichlorophenyl)-3-quinolin-4-ylurea

From 3,4-dichlorophenyl isocyanate (0.113 g) and D4 (0.072 g) the title compound (0.112 g) was prepared according to the method of Example 15.

$^1$H NMR δ: 7.40 (1H, dd), 7.61 (1H, d), 7.72 (1H, t), 7.81 (1H, t), 7.99–8.05 (2H, m), 8.21 (2H, m), 8.77 (1H, d), 9.35 (1H, s), 9.60 (1H, s).

m/z (API$^+$): 332, 334 (MH$^+$).

27. 1-(3-Carboethoxyphenyl)-3-quinolin-4-ylurea Hydrochloride

From 3-carboethoxyphenyl isocyanate (0.096 g) and D4 (0.072 g) the title compound (0.027 g) was prepared according to the method of Example 15.

$^1$H NMR δ: 1.35 (3H, t), 4.35 (2H, q), 7.54 (1H, t), 7.69 (1H, d), 7.78 (1H, d), 7.94 (1H, t), 8.09–8.18 (2H, m), 8.28 (1H, s), 8.73 (1H, d), 9.01–9.05 (2H, m), 11.02 (1H, s), 11.13 (1H, s).

m/z (API$^+$): 336 (MH$^+$).

28. 1-(3-Bromo-4-methoxyphenyl)-3-quinolin-4-ylurea hydrochloride

D3 (0.203 g) in toluene (10 ml) was warmed to 75° C. for 1 h and then to 100° C. for 1 h. The reaction mixture was cooled to room temperature and 3-bromo-4-methoxyaniline (H. Mitchell et al, *J. Org. Chem.*, 1994, 59, 682) (0.202 g) added in dichloromethane (5 ml). The mixture was stirred overnight and the solvent decanted. The solid was suspended in methanol (10 ml) and excess ethereal HCl (1M) added.

The solid was collected by filtration and the residue washed with methanol and diethyl ether to give the title compound (0.20 g).

$^1$H NMR δ: 3.65 (3H, s), 6.93 (1H, d, J 9 Hz), 7.20 (1H, dd, J 3+9 Hz), 7.54 (1H, t, J 7 Hz), 7.66 (1H, 8 Hz), 7.72 (1H, d, J 3 Hz), 8.82 (1H, d, J 8 Hz), 8.12 (1H, d, J 5.6 Hz), 8.21 (1H, d, J 8 Hz), 8.59 (1H, d, J 5.5 Hz), 9.54 (2H, s).

m/z (API$^+$): 372, 374 (MH$^+$).

29. 1-(4-Trifluoromethylthiophenyl)-3-quinolin-4-ylurea hydrochloride

From 4-trifluoromethylthioaniline (0.193 g) and D3 (0.198 g) the title compound (0.14 g) was prepared according to the method of Example 28.

$^1$H NMR δ: 7.74 (4H, s), 7.93 (1H, t), 8.08–8.19 (2H, m), 8.71 (1H, d), 9.02 (1H, d), 9.07 (1H, d), 11.11 (1H, bs), 11.39 (1H, s).

m/z (API$^+$): 364 (MH$^+$).

30. 1-(8-Oxo-5,6,7,8-tetrahydronaphthalen-2-yl)-3-quinolin-4-ylurea hydrochloride From 7-amino-3,4-dihydro-2H-naphthalen-1-one (0.161 g) and D3 (0.198 g) the title compound (0.14 g) was prepared according to the method of Example 28.

$^1$H NMR δ: 2.03–2.09 (2H, m), 2.62 (2H, t), 2.92 (2H, t), 7.38 (1H, d), 7.69 (1H, dd), 7.92 (1H, t), 8.08–8.17 (3H, 8.73 (1H, d), 9.01 (1H, d), 9.08 (1H, d), 11.08 (1H, s), 11.12 (1H, s).

m/z (API$^+$): 332 (MH$^+$).

31. 1-(3-Chloro-4-methoxyphenyl)-3-quinolin-4-ylurea hydrochloride

From 3-chloro-4-methoxyaniline (0.082 g) and D3 (0.095 g) the title compound (0.12 g), after trituration with methanol, was prepared according to the method of Example 28.

$^1$H NMR (CD$_3$OD) δ: 3.98 (3H, s), 7.17 (1H, d), 7.49 (1H, dd), 7.82 (1H, d), 8.03 (1H, m), 8.19 (2H, m), 8.61(1H, d), 8.93 (2H, s).

32. 1-(4-N-Morpholin-4-ylphenyl)-1-quinolin-4-ylurea dihydrochloride

D4 (0.231 g) was added in portions to carbonyl diimidazole (0.259 g) in dichloromethane (20 ml) and the mixture stirred at room temperature for 2 h. Solvent was removed at reduced pressure and dimethylformamide (8 ml) and 4-morpholinoaniline (0.285 g) added. The mixture was heated at 100° C. for 1 h, cooled to room temperature and poured into water. The precipitated solid was collected by filtration and washed with water, diethyl ether and hexane. The solid was suspended in methanol and treated with excess ethereal HCl (1M). The mixture was stirred for 15 min, filtered, the residue washed with methanol, dissolved in hot ethanol (150 ml), filtered and solvent volume reduced to (75 ml). The crystallised solid was collected by filtration and washed with methanol to give the title compound (0.185 g).

$^1$H NMR (d$_6$-DMSO and D$_2$O) δ: 3.39 (4H, bs), 3.93 (4H, bs), 7.44 (2H, d), 7.60 (2H, d), 7.92 (1H, t), 8.07–8.19 (2H, m), 8.73 (1H, d), 8.97 (1H, d), 9.06 (1H, d).

m/z (API$^+$): 349 (MH$^+$).

33. 1-(3-Acetylphenyl)-3-quinolin-4-ylurea hydrochloride

A mixture of D4 (0.100 g) and 3-acetylphenyl isocyanate (0.112 g) in toluene/dichloromethane (12 ml, 1:2) containing 4-dimethylaminopyridine (0.002 g) was stirred at room temperature for 16 h. The precipitated solid was separated by filtration, suspended in ethyl acetate and excess ethereal HCl (1M) added. The precipitated pale yellow title compound (0.027 g) was separated by filtration.

$^1$H NMR δ: 2.60 (3H, s), 7.55 (1H, t), 7.72–7.81 (2H, m), 7.93 (1H, t), 8.08–8.20 (3H, m), 8.73 (1H, d), 9.01 (1H, d), 9.06 (1H, d), 11.06 (1H, d), 11.17 (1H, s).

m/z (API$^+$): 306 (MH$^+$).

34. 1-(4-Phenylaminophenyl)-3-quinolin-4-ylurea dihydrochloride

D4 (0.192 g) in dichloromethane (5 ml) was added dropwise to a stirred suspension of carbonyl diimidazole (0.169 g) in dichloromethane (5 ml). After 30 min solvent was removed at reduced pressure and dimethylformamide (8 ml) and 4-aminodiphenylamine (0.192 g) added. The mixture was heated for 30 min at 95° C. cooled to room temperature and poured into water (150 ml). The black oil obtained was triturated with methanol to give a grey solid which was suspended in methanol and excess ethereal HCl (1M) added to give the title compound (0.212 g).

$^1$H NMR δ: 6.79 (1H, t), 7.02–7.25 (6H, m), 7.46 (2H, d), 7.91 (1H, t), 8.08–8.20 (2H, m), 8.75 (1H, d), 8.97 (1H, d), 9.17 (1H, d), 10.96 (1H, d), 11.17 (1H, s).

m/z (API$^+$): 355 (MH$^+$).

35. 1-[3-Oxazo-5-yl)phenyl]-3-quinolin-4-ylurea

From D4 (0.20 g) and 3-(1,3-oxazol-5-yl)aniline (0.222 g), the title compound (0.135 g), following recrystallisation from methanol, was prepared according to the method of Example 34.

$^1$H NMR δ: 7.39–7.46 (3H, m), 7.67–7.72 (2H, m), 7.79 (1H, t), 7.96–8.02 (2H, m), 8.25 (2H, m), 8.49 (1H, s), 8.48 (1H, d), 9.31 (1H, bs), 9.49 (1H, bs).

m/z (API$^+$): 331 (MH$^+$).

36. 1-[4-((4,6-Dimethylpyrimidin-2-yl)methylamino)phenyl]-3-quinolin-4-ylurea dihydrochloride From D4 (0.10 g) and N-methyl-N-(4,6-dimethylpyrimidin-2-yl)-1,4-phenylenediamine (0.158 g), followed by column chromatography (silica gel, 1:1 ethyl acetate/hexane→ethyl acetate), combining the appropriate fractions and removing the solvent under reduced pressure, the title compound (0.057 g) was prepared according to the method of Example 34.

$^1$H NMR δ: 2.34 (6H, s), 2.51 (3H, s), 6.73 (1H, s), 7.40 (2H, d), 7.65 (2H, d), 7.92 (1H, t), 8.13 (1H, t), 8.24 (1H, d), 8.77 (1H, d), 9.01 (1H, d), 9.28 (1H, d), 11.36 (1H, s), 11.52 (1H, s).

m/z (API$^+$): 399 (MH$^+$).

37. 1-(4-Pyrrolidinylphenyl-3-quinolin-4-ylurea dihydrochloride

From D4 (0.10 g) and 4-pyrrolidinylaniline (0.112 g) the title compound (0.078 g) was prepared according to the method of Example 34.

$^1$H NMR δ: 2.00 (4H, m), 3.34 (4H, m), 6.88 (2H, bs), 7.47 (2H, d), 7.90 (1H, t), 8.08–8.20 (2H, m), 8.74 (1H, d), 8.96 (1H, d), 9.17 (1H, d), 10.93 (1H, bs), 11.16 (1H, s).

m/z (API$^+$): 333 (MH$^+$).

38. 1-(3-Dimethylaminophenyl)-3-quinolin-4-ylurea dihydrochloride

From D4 (0.10 g) and N,N-dimethylbenzene-1,3-diamine (0.095 g), the title compound (0.014 g) after column chromatography (silica gel, 1:1 ethyl acetate/hexane→ethyl acetate) was prepared according to the method of Example 34.

$^1$H NMR δ: 2.93 (6H, s), 6.86 (1H, bd), 7.10 (1H, d), 7.26 (1H, t), 7.38 (1H, bs), 7.82 (1H, t), 7.99–8.11 (2H, m), 8.65 (1H, d), 8.88 (1H, d), 9.06 (1H, d), 11.11 (2H, bs).

m/z (API$^+$): 307 (MH$^+$).

39. 1-(4-Carboxamidophenyl)-3-quinolin-4-ylurea hydrochloride

From D4 (0.10 g) and 4-aminobenzamide (0.095 g), followed by column chromatography (silica gel, 1:1 ethyl acetate/hexane ethyl acetate), the title compound (0.09 g) was prepared according to the method of Example 34.

$^1$H NMR δ: 7.30 (1H, bs), 7.64 (2H, d), 7.91 (4H, d), 8.09–8.19 (2H, m), 8.73 (1H, d), 9.03 (1H, d), 9.06 (1H, d), 11.08 (1H, bs), 11.20 (1H, s).

m/z (API$^+$): 307 (MH$^+$).

40. 1-(4-N,N-Diethylaminophenyl)-3-quinolin-4-ylurea dihydrochloride

From D4 (0.085 g) and N,N-diethylbenzene-1,4-diamine (0.097 g), the title compound (0.04 g) was prepared according to the method of Example 34.

$^1$H NMR δ: 1.05 (6H, t), 3.52 (4H, obscured by HOD resonance), 7.76 (4H, bs), 7.93 (1H, t), 8.12 (1H, t), 8.20 (1H, d), 8.74 (1H, d), 9.02 (1H, d), 9.19 (1H, d), 11.29 (1H, bs), 11.59 (1H, bs), 12.36 (1H, bs).

m/z (API$^+$): 335 (MH$^+$).

41. 1-(4-Dimethylaminophenyl)-3-(5-methoxyquinolin-4-yl)urea dihydrochloride A solution of D15 (0.143 g) in dichloromethane (4 ml) was treated with 4-dimethylaminophenyl isocyanate (0.133 g, 0.58 mmol) in toluene (4 ml). The reaction was stood at room temperature for 16 h, solvent removed at reduced pressure and the residue precipitated from dichloromethane solution (5 ml) with diethyl ether (20 ml). The precipitated compound (free base) was separated by filtration and suspended in methanol. The HCl salt was prepared to give the title compound (0.150 g).

$^1$H NMR δ: (free base) 2.87 (6H, s), 3.97 (3H, bs), 6.75 (2H, d), 7.04 (1H, d), 7.30 (2H, d), 7.50–7.63 (2H, m), 8.32 (1H, d), 8.59 (1H, d), 9.47 (1H, bs), 10.01 (1H, s).

m/z (API$^+$): 295 (MH$^+$).

42. 1-(4-Dimethylaminophenyl)-3-(8-bromoquinolin-4-yl)urea dihydrochloride

D17 (0.25 g) in toluene (15 ml) was heated at 75° C. for 2 h. The mixture was cooled to room temperature and N,N-dimethylbenzene-1,4-diamine (0.122 g) in dichloromethane (5 ml) added. After stirring for 16 h, the precipitated solid was collected by filtration to give the title compound (free base). The HCl salt was prepared to give the title compound.

$^1$H NMR δ: 3.04 (6H, s), 7.59–7.71 (5H, m), 8.33 (1H, d), 8.67 (1H, d), 8.85 (1H, d), 9.13 (1H, d) 11.17 (1H, s), 11.47 (1H, s).

m/z (API$^+$): 385, 387 (MH$^+$).

43. 1-(4-Dimethylaminophenyl)-3-(8-methoxyquinolin-4-yl)urea dihydrochloride From D23 (0.087 g) and 4-dimethylaminophenyl isocyanate (0.089 g) the title compound (0.080 g) was prepared according to the method of Example 41.

$^1$H NMR δ: 3.08 (6H, s), 4.15 (3H, s), 7.56–7.68 (5H, m), 7.84 (1H, t), 8.73–8.84 (3H, m), 11.21 (1H, s), 11.52 (1H, bs).

m/z (API$^+$): 337 (MH$^+$).

44. 1-(2-Chlorophenyl)-3-quinolin-4-ylurea

From 2-chlorophenyl isocyanate (0.077 g) and D4 (0.072 g) the title compound (0.065 g) was prepared according to the method of Example 15.

$^1$H NMR δ: 7.09 (1H, t), 7.34 (1H, t), 7.50 (1H, d), 7.66 (1H, t), 7.77 (1H, t), 7.98 (1H, d), 8.16 (1H, d), 8.20 (1H, d), 8.29 (1H, d), 8.72 (1H, d), 9.10 (1H, s), 9.81 (1H, s).

m/z (API$^+$): 298, 300 (MH$^+$).

45. 1-(2-Methylphenyl)-3-quinolin-4-ylurea

From 2-methylphenyl isocyanate (0.067 g) and D4 (0.072 g) the title compound (0.086 g) was prepared according to the method of Example 15.

1H NMR δ: 2.16 (3H, s), 6.92 (1H, t), 7.04–7.15 (2H, m), 7.58 (1H, t), 7.68 (1H, t), 7.76 (1H, d), 7.90 (1H, d), 8.13 (1H, d), 8.18 (1H, d), 8.54 (1H, s), 8.62 (1H, d), 9.93 (1H, s).

m/z (API$^+$): 278 (MH$^+$).

46. 1-(4-Methoxy-2-methylphenyl)-3-quinolin-4-ylurea hydrochloride

4-Methoxy-2-methyl aniline in tetrahydrofuran (10 ml) was added to a stirred suspension of carbonyl diimidazole (0.26 g) in tetrahydrofuran (10 ml). After stirring for 1 h, solvent was removed at reduced pressure, the residue dissolved in dimethylformamide (8 ml) and 4-aminoquinoline (0.23 g) added. The mixture was heated at 95° C. for 30 min, cooled and poured into water and extracted with dichloromethane (2×20 ml). The combined organic phase was washed with water, dried (Na$_2$SO$_4$) and solvent removed at reduced pressure. The residue was column chromatographed (silica gel ethyl acetate/hexane mixture) to give, after conversion to the hydrochloride salt the title compound (0.02 g).

$^1$H NMR δ: 2.33 (3H, s), 3.75 (3H, s), 6.80 (1H, dd, J 2.54+11 Hz), 6.85 (1H, m), 7.50 (1H, d, J 8.7 Hz), 7.89–7.95 (1H, m), 8.08–8.18 (2H, m), 8.71 (1H, d, J 6.8 Hz), 8.97 (1H, d, J 6.8 Hz), 9.13 (1H, d, J 8.7 Hz), 9.92 (1H, bs), 11.23 (1H, bs).

m/z (API$^+$): 308 (MH$^+$).

47. 1-(1-Hydroxy-1-ethylphen-3-yl)-3-quinolin-4-ylurea hydrochloride

Example 33 (0.460 g) in ethanol/water 10%, 40 ml) was treated with sodium borohydride (0.126 g). The mixture was stirred at room temperature overnight, acidified cautiously with HCl (5M), neutralised with sodium carbonate and solvent removed at reduce pressure. The residue was triturated with water, filtered, dried and converted to the title compound HCl salt (0.27 g) according to the method of Example 46.

$^1$H NMR δ: 1.34 (3H, d), 4.72 (1H, q), 5.22 (1H, bs), 7.01 (1H, d), 7.31 (1H, t), 7.42 (1H, d), 7.51 (1H, s), 7.68 (1H, t), 7.78 (1H, t), 7.99 (1H, d), 8.23–8.26 (2H, m), 8.73 (1H, d), 9.35 (2H, bs).

m/z (API$^+$): 308 (MH$^+$).

48. 1-(3-Trifluoromethylthiophenyl)-3-quinolin-4-ylurea hydrochloride

From 3-trifluoromethylthiophenyl isocyanate (0.152 g) and D4 (0.100 g) the title compound was prepared according to the method of Example 15 (0.105 g).

¹H NMR δ: 7.45 (1H, d), 7.56 (1H, t), 7.71 (1H, d), 7.93 (1H, t), 8.06–8.19 (3H, m), 8.73 (1H, d), 9.025 (1H, d), 9.10 (1H, d), 11.13 (1H, bs), 11.39 (1H, bs).

m/z (API⁺): 364 (MH⁺).

49. 1-(3,5-Dichlorophenyl)-3-quinolin-4-ylurea hydrochloride

From 3,5-dichlorophenyl isocyanate (0.188 g) and D4 (0.144 g) the title compound (0.130 g) was prepared according to the method of Example 15.

¹H NMR δ: 7.31 (1H, m), 7.60 (2H, m), 7.93 (1H, t), 8.08–8.24 (2H, m), 8.70 (1H, d), 9.03–9.12 (2H, m), 11.12 (1H, bs), 11.59 (1H, bs).

m/z (API⁺): 332, 334 (MH⁺).

50. 1-(1-Methylbenzimidazol-6-yl)-3-quinolin-4-ylurea dihydrochloride

A mixture of 1-methyl-6-benzimidazole carboxylic acid (0.230 g), triethylamine (0.17 ml) and diphenyl phosphoryl azide (0.33 g) were combined in toluene (10 ml) and warmed to 65° C. for 30 min. D4 (0.17 g) was added and heating continued at 65° C. for 16 h. Solvent was removed at reduced press,re and the residue column chromatographed (silica gel (20%→100% ethyl acetate/pentane) to give after conversion to the HCl salt the title compound (0.050 g).

1H NMR δ: 4.05 (3H, s), 7.57 (1H, d, J 2+9 Hz), 7.90 (2H, m), 8.12 (1H, dd, J 7+7 Hz), 8.29 (2H, m), 8.79 (1H, d, J 7 Hz), 9.02 (1H, d, J 7 Hz), 9.32 (1H, d, J 9 Hz), 9.44 (1H, s), 11.47 (1H, s), 11.93 (1H, s).

m/z (API⁺): 317 (MP⁺).

51. 1-(4-Methoxy-3-trifluoromethylphenyl)-3-quinolin-4-ylurea hydrochloride

From D3 (0.198 g) and 4-methoxy-3-trifluoromethylaniline (0.191 g) the title compound (0.218 g) was prepared according to the method of Example 28.

1H NMR δ: 3.69 (3H, s), 7.12 (1H, d), 7.51 (1H, dd), 7.70–7.54 (2H, m), 7.88–7.98 (2H, m), 8.52 (1H, d), 8.80 (1H, d), 8.89 (1H, d), 10.89 (1H, s), 10.99 (1H, d).

m/z (API⁺): 362 (MH⁺).

52. N-Methyl-3-(3-quinolin-4-ylureido)benzamide hydrochloride

From D3 (0.198 g) and 3-N-methylcarboxamidoaniline (0.191 g) the title compound salt (0.160 g) was prepared according to the method of Example 28.

¹H NMR δ: 2.80 (3H, d), 7.45 (1H, t), 7.54 (1H, d), 7.71 (1H, d), 7.91 (1H t), 8.05–8.24 (3H, m), 8.50 (1H, d), 8.76(1H, d), 9.01 (1H, d), 9.17 (1H, d), 11.23 (1H, s), 11.26 (1H, s).

m/z (API⁺): 321 (MH⁺).

53. 1-(4-Dimethylaminomethylphenyl)-3-quinolin-4-ylurea dihydrochloride

From D3 (0.15 g) and N,N-dimethylbenzene-1,4-diamine (0.113 g) the title compound (0.125) was prepared according to the method of Example 28.

¹H NMR δ: 2.41 (6H, s), 3.88 (2H, s), 7.46 (2H, d), 7.60 (2H, d), 7.93 (1H, t), 8.09–8.19 (2H, m), 8.74 (1H, d), 9.00 (1H, d), 9.10 (1H, d), 11.11 (1H, s), 11.14 (1H, s).

m/z (API⁺): 321 (MH⁺).

54. 1-(4-Hydroxymethylphenyl)-3-quinolin-4-ylurea hydrochloride

From D3 (0.198 g) and 4-aminobenzyl alcohol (0.124 g) the title compound (0.096 g) was prepared according to the method of Example 28.

¹H NMR δ: 4.47 (2H, s), 7.32 (2H, d), 7.54 (2H, d), 7.92 (1H, t), 8.08–8.21 (2H, m), 8.73 (1H, d), 8.99 (1H, d), 9.09 (1H, d), 10.96 (1H, s), 11.08 (1H, s).

m/z (API⁺): 294 (MH⁺).

55. 1-(4-N,N-Dimethylaminophenyl)-3-(7-methoxy)quinolin-4-ylurea hydrochloride From 4-N,N-dimethylaminophenyl isocyanate (0.089 g) and 4-amino-7-methoxyquinoline (Spaeth et al, *Chem. Ber.*, 1924, 57, 1250) (0.087 g) the title compound (0.044 g), after column chromatography (silica gel, 20→100% ethyl acetate/hexane eluant) and conversion to the HCl salt, was prepared according to the method of Example 15.

¹H NMR δ: 3.08 (6H, s), 4.00 (3H, s), 7.51–7.66 (6H, m), 8.59 (1H, d, J 6.9 Hz), 8.87 (1H, d, J 6.9 Hz), 9.10 (1H, d, J 9.3 Hz), 11.18 (1H, bs), 11.30 (1H, bs).

m/z (API⁺): 337 (MH⁺).

56. 1-(3-Fluoro-4-methoxyphenyl)-3-quinolin-4-ylurea hydrochloride

From D3 (0.100 g) and 3-fluoro-4-methoxyaniline (0.073 g) the title compound (0.056 g) was prepared according to the method of Example 28.

¹H NMR δ: 3.83 (3H, s), 7.15–7.22 (2H, m), 7.57 (1H, d), 7.90–7.96 (1H, m), 8.08–8.17 (2H, m), 8.69 (1H, d), 8.99 (2H, d), 10.86 (1H, s), 10.93 (1H, s)

m/z (API⁺): 312 (MH⁺).

57. 1-(3,4-Dihydro-2H-benzo[b][1,4]dioxepin-7-yl)-3-quinolin-4-ylurea hydrochloride From D3 (0.100 g) and 3,4-dihydro-2H-benzo[b][1,4]dioxepin-7-ylamine (0.094 g) the title compound (0.087 g) was prepared according to the method of Example 28.

¹H NMR δ: 2.10 (2H, m), 4.07–4.16 (4H, m), 6.97 (1H, d), 7.10 (1H, dd), 7.27 (1H, d), 7.88–7.94 (1H, m), 8.08–8.18 (2H, m), 8.71 (1H, d), 8.98 (1H, d), (1H, d), 10.99 (1H, s), 11.06 (1H, s).

m/z (API⁺): 336 (MH⁺).

58. 1-(3-Chloro-4-dimethylaminophenyl)-3-quinolin-4-ylurea dihydrochloride

From D3 (0.198 g) and 3-chloro-4-N,N-dimethylbenzene-1,4-diamine (0.170 g) the title compound (0.190 g) was prepared according to the method of Example 28.

¹H NMR δ: 2.86 (6H, s), 7.41–7.50 (2H, m), 7.77 (1H, d), 7.91 (1H, t), 8.12 (1H, t), 8.21 (1H, d), 8.74 (1H, d), 9.00 (1H, d), 9.22 (1H, d), 11.29 (1H, bs), 11.55 (1H, bs).

m/z (API⁺): 341, 343 (MH⁺).

59. 1-Quinolin-4-yl-3-(4-[1,2,4]triazol-1-ylphenyl)urea hydrochloride

From D3 (0.099 g) and 4-[1,2,4-triazol-1-yl]aniline (0.080 g) the title compound (0.108 g) was prepared according to the method of Example 28.

¹H NMR δ: 7.76 (2H, d, J 9 Hz), 7.87–7.96 (3H, m), 8.09–8.25 (3H, m), 8.77 (1H, d, J 7 Hz), 9.03 (1H, d, J 7 Hz), 9.24 (1H, d, J 9 Hz), 9.29 (1H, s), 11.32 (1H, s), 11.55 (1H, s).

m/z (API⁺): 331 (MH⁺).

60. 1-(Benzothiazol-6-yl)-3-quinolin-4-ylurea hydrochloride

From D3 (0.099 g) and 6-aminobenzothiazole (0.78 g) the title compound (0.10 g) was prepared according to the method of Example 28.

$^1$H NMR δ: 7.60 (1H, dd), 7.78 (1H, t), 7.92 (1H, t), 8.04–8.09 (2H, m), 8.40–8.48 (2H, m), 8.58 (1H, d), 8.86 (1H, d), 9.28 (1H, s), 10.07 (1H, bs), 10.32 (1H, s).

m/z (API$^+$): 321 (MH$^+$).

61. 1-Benzo[b]thiophen-5-yl-3-quinolin-4-ylurea hydrochloride

From D3 (0.198 g) and 5-aminobenzthiophene sulphate salt (0.149 g) the title compound (0.100 g) was prepared according to the method of Example 28 except that triethylamine (0.165 ml) was added to the reaction mixture with the 5-aminobenzthiophene sulphate.

$^1$H NMR δ: 7.42–7.48 (2H, m), 7.75–7.80 (2H, m), 7.89 (1H, t), 7.97 (1H, d), 8.03 (1H, d), 8.20 (1H, d), 8.30–8.39 (2H, m), 8.82 (1H, d), 9.56 (2H, bs).

m/z (API$^+$): 320 (MH$^+$).

62. 1-(1-Methyl-1,2,3,4-tetrahydroquinolin-6-yl-3-quinolin-4-ylurea dihydrochloride From D3 (0.089 g) and 1-methyl-6-amino-1,2,3,4-tetrahydroquinoline dihydrochloride (0.089 g) the title compound (0.090 g) was prepared according to the method of Example 28 except that triethylamine (0.09 g) was added to the reaction mixture with the 1-methyl-6-amino-1,2,3,4-tetrahydroquinoline dihydrochloride.

$^1$H NMR δ: 2.04 (2H, m), 2.83 (2H, m), 3.03 (3H, s), 3.37 (2H, m), 7.20 (1H, bs), 7.35 (1H, s), 7.43 (1H, d), 7.90 (1H, s), 8.11 (1H, t), 8.20 (1H, d), 8.74 (1H, d), 8.98 (1H, d), 9.23 (1H, d), 11.29 (2H, s).

m/z (API$^+$): 333 (MH$^+$).

63. 1-(4-N-Ethyl-N-isopropylaminophenyl)-3-quinolin-4-ylurea dihydrochloride From D3 (0.198 g) and N-ethyl-N-isopropylbenzene-1,4-diamine hydrochloride (0.215 g) the title compound (0.290 g) was prepared according to the method of Example 28 except that triethylamine (0.100 g) was added to the reaction mixture with the N-ethyl-N-isopropylbenzene-1,4-diamine hydrochloride.

$^1$H NMR δ: (free base) 1.03 (3H, t), 1.07 (6H, d), 3.14 (2H, q), 3.93 (1H, m), 6.69 (2H, d), 7.26 (2H, d), 7.62 (1H, t), 7.72 (1H, t), 7.92 (1H, dd), 8.15–8.21 (2H, m), 8.65 (1H, d), 8.91 (1H, s), 9.09 (1H, s).

m/z (API$^+$): 349 (MH$^+$).

64. 1-(4-Methyl-3,4-dihydro-2H-benzo[1,4]oxazin-7-yl)-3-quinolin-4-ylurea dihydrochloride From D3 (0.150 g) and 4-methyl-7-amino-3,4-dihydro-(1,4)-benzoxazine (0.124 g) (D. R. Shridhar, M. Jogibhukta, V. S. Krishnan; Org. Prep. Proced. Int. 1982, 14, 195) the title compound (0.186 g) was prepared according to the method of Example 28.

$^1$H NMR δ: 2.85 (3H, s), 3.24 (2H, m), 4.28 (2H, m), 6.78 (1H, d), 6.95 (1H, dd), 7.05 (1H, d), 7.90 (1H, t), 8.11 (1H, t), 8.18 (1H, d), 8.72 (1H, d), 8.95 (1H, d), 9.17 (1H, d), 10.91 (1H, s), 11.14 (1H, s).

m/z (API$^+$): 335 (MH$^+$).

65. 1-(2-Methyl-1,2,3,4-tetrahydro-isoquinolin-7-yl)-3-quinolin-4-yl urea hydrochloride From D3 (0.10 g) and 2-methyl-7-amino-1,2,3,4-tetrahydroisoquinoline (0.081 g) the title compound (0.095 g) was prepared according to the method of Example 28.

$^1$H NMR δ: 2.90 (3H, d), 3.03–3.39 (4H, m), 4.23–4.55 (2H, m), 7.26 (1H, d), 7.44–7.49 (2H, m), 7.91 (1H, t), 8.12 (1H, t), 8.22 (1H, d), 8.74 (1H, d), 9.00 (1H, d), 9.27 (1H, d), 11.35 (1H, s), 11.45 (1H, s).

m/z (API$^+$): 333 (MH$^+$).

66. 1-(1,2-Dimethyl-1H-indol-5-yl)-3-quinolin-4-ylurea hydrochloride

From D3 (0.321 g) and 5-amino-1,2-dimethylindole (0.272 g) the title compound (0.262 g) was prepared according to the method of Example 28.

$^1$H NMR δ: 2.39 (3H, s), 3.65 (3H, s), 6.18 (1H, s), 7.11 (1H, dd), 7.33 (1H, d), 7.64–7.70 (2H, m), 7.77 (1H, t), 7.97 (1H, d), 8.22–8.27 (2H, m), 8.71 (1H, d), 9.10 (1H, s), 9.18 (1H, s).

m/z (API$^+$): 331 (MH$^+$).

67. 1-(2,3-Dihydro-1H-indol-5-yl)-3-quinolin-4-yl urea dihydrochloride a) From D3 (0.50 g) and 5-amino-1-tert-butoxycarbonylindoline (0.565 g) 5-(3-quinolin-4-ylureido)-2,3-dihydroindole-1-carboxylic acid tert butyl ester (0.79 g) was prepared according to the method of Example 28.

m/z (API$^+$): 405 (MH$^+$).

b) 5-(3-Quinolin-4-ylureido)-2,3-dihydroindole-1-carboxylic acid tert butyl ester (0.10 g) in methanol (4 ml) was treated with 1M HCl in diethyl ether (1 ml) and stirred for 1 hr. Additional HCl (2 ml, 1M in diethyl ether) was added followed by a further aliquot (2 ml) after 20 h. The mixture was stirred for a further 6 hr and solvent removed at reduced pressure. The product was triturated with methanol (50 ml) and the solid collected by filtration to give the title compound (0.045 g).

$^1$H NMR δ: 3.23 (2H, t), 3.73 (2H, t), 7.40 (1H, d), 7.53 (1H, dd), 7.70 (1H, s), 7.91 (1H, t), 8.12 (1H, t), 8.19 (1H, d), 8.73 (1H, d), 9.01 (1H, d), 9.21 (1H, d) 11.27 (1H, s), 11.48 (1H, s).

m/z (API$^+$): 305 (MH$^+$).

68. 1-(4-Dimethylaminophenyl)-3-(7-bromoquinolin-4-yl)urea dihydrochloride

From D25 (0.217 g) and N,N-dimethylbenzene-1,4-diamine (0.106 g) the title compound (0.260 g) was prepared according to the method of Example 28.

$^1$H NMR δ: 3.08 (6H, s), 7.52 (2H, bs), 7.62 (2H, d), 8.10 (1H, dd), 8.39 (1H, d), 8.71 (1H, d), 9.00 (1H, d), 9.10 (1H, d), 11.24 (1H, bs), 11.30 (1H, s).

m/z (API$^+$): 385, 387 (MH$^+$).

69. 1-(4-Dimethylaminophenyl)-3-(6-bromoquinolin-4-yl)urea dihydrochloride

From D27 (0.20 g) and N,N-dimethylamino-benzene-1,4-diamine (0.98 g) the title compound (0.170 g) was prepared according to the method of Example 28.

$^1$H NMR δ: (2.86, 6H, s), 6.74 (2H, d), 7.34 (2H, d), 7.85–7.96 (2H, m), 8.27 (1H, d), 8.47 (1H, d), 8.72(1H, d), 8.92 (1H, s), 9.17 (1H, s).

m/z (API$^+$): 385, 387 (MH$^+$).

70. 1-(3-Ethoxyphenyl)-3-quinolin-4-ylurea hydrochloride

From 3-ethoxybenzoic acid (0.115 g) and D4 (0.10 g) the title compound (0.040 g) was prepared according to the method of Example 50.

¹H NMR δ: 1.35 (3H, t, J 7 Hz), 4.03 (2H, q, J 7 Hz), 6.67 (1H, dd, J 2+8 Hz), 7.08 (1H, d, J 8 Hz), 7.26 (2H, m), 7.92 (1H, m), 8.13 (2H, m), 8.73 (1H, d, J 7 Hz), 9.00 (1H, d, J7 Hz), 9.12 (1H, d, J8 Hz), 11.05 (1H, s), 11.09 (1H, s).

m/z (API⁺): 308 (MH⁺).

71. 1-(4-Ethylthiophenyl)-3-quinolin-4-yl urea hydrochloride

From 4-ethylthiobenzoic acid (0.186 g) and D4 (0.144 g) the title compound (0.130 g) was prepared to the method of Example 50.

¹H NMR δ: 1.22 (3H, t, J 7 Hz), 2.95 (2H, q, J 7 Hz), 7.37 (2H, d, J 8 Hz), 7.56 (2H, d, J 8 Hz), 7.92 (1H, m), 8.13 (2H, m), 8.72 (1H, d, J 7 Hz), 9.00 (1H, d, J 7 Hz), 9.06 (1H, d, J 9 Hz), 10.99 (1H, s), 11.03 (1H, s).

m/z (API⁺): 324 (MH⁺).

72. 1-(3-Bromo-4-dimethylaminophenyl)-3-quinolin-4-ylurea-dihydrochloride

From 3-bromo-4-dimethylaminobenzoic acid (0.200 g) and D4 (0.132 g) the title compound (0.145 g) was prepared according to the method of Example 50.

¹NMR δ: 2.83 (6H, s), 7.42 (1H, d, J 9 Hz), 7.53 (1H, dd, J 2+9 Hz), 7.91 (2H, m), 8.12 (1H, dd, J 7+7 Hz), 8.23 (1H, d, J 8 Hz), 8.74 (1H, d, J 7 Hz), 9.01 (1H, d, J 7 Hz), 9.24 (1H, d, J 8 Hz), 11.30 (1H, s), 11.55 (1H, s).

m/z (API⁺): 385, 387 (MH⁺).

73. 1-(4-Methoxy-3-methylphenyl)-3-quinolin-4-ylurea hydrochloride

From 4-methoxy-3-methylbenzoic acid (0.200 g) and D4 (0.144 g) the title compound (0.130 g) was prepared according to the method of Example 50.

¹H NMR δ: 2.16 (3H, s), 3.78 (3H, s), 6.93 (1H, d, J 9 Hz), 7.32 (1H, d, J 2 Hz), 7.39 (1H, dd, J 2+9 Hz), 7.90 (1H, m), 8.14 (2H, m), 8.73 (1H, d, J 7 Hz), 8.97 (1H, d, J 7 Hz), 9.13 (1H, d, J 9 Hz), 10.81 (1H, s), 11.09 (1H, s).

m/z (API⁺): 308 (MH⁺).

74. 1-(4-Methoxy-3-prop-2-(enylphenyl)-3-quinolin-4-yl hydrochloride

From 4-methoxy-3-prop-2-enylbenzoic acid (0.251 g) and D4 (0.210 g) the title compound (0.092 g) was prepared according to the method of Example 50.

¹H NMR δ: 3.33 (2H, d, J 6 Hz), 3.78 (3H, s), 5.08 (2H, m), 5.87–6.01 (1H, m), 6.99 (1H, d, J 1Hz), 7.33 (1H, d, J 2 Hz), 7.42 (1H, dd, J 2+9 Hz), 7.92 (1H, m), 8.12 (2H, m), 8.73 (1H, d, J 7 Hz), 8.97 (1H, d, J 7 Hz), 9.07 (1H, d, J 9 Hz), 10.72 (1H, s), 11.00 (1H, s).

m/z (API⁺): 334 (MH⁺).

75. 1-(3-Ethyl-4-methoxyphenyl)-3-quinolin-4-ylurea hydrochloride

From 3-ethyl-4-methoxybenzoic acid (0.200 g) and the D4 (0.19 g) the title compound (0.160 g) was prepared according to the method of Example 50.

¹H NMR δ: 1.15 (3H, t, J 8 Hz), 2.58 (2H, q, J 8 Hz), 3.79 (3H, s), 6.96 (1H, d, J 9 Hz), 7.33 (1H, d, J 2 Hz), 7.40 (1H, dd, J 2+9 Hz), 7.91 (1H, m), 8.14 (2H, m), 8.74 (1H, d, J 7 Hz), 8.97 (1H, d, J 7 Hz), 9.13 (1H, d, J 9 Hz), 10.82 (1H, s), 11.08 (1H, s).

m/z (API⁺): 322 (MH⁺).

76. 1-(3-Acetyl-4-methoxyphenyl)-3-quinolin-4-ylurea hydrochloride

From 3-acetyl-4-methoxybenzoic acid (0.150 g) and D4 (0.11 g) the title compound (0.080 g) was prepared according to the method of Example 50.

¹H NMR δ: 2.56 (3H, s), 3.90 (3H, s), 7.22 (1H, d, J 9 Hz), 7.70 (1H, dd, J 2+9 Hz), 7.80 (1H, d, J 2 Hz), 7.90 (1H, m), 8.14 (2H, m), 8.73 (1H, d, J 7 Hz), 8.99 (1H, d, J7 Hz), 9.13 (1H, d, J9 Hz), 11.09 (1H, s), 11.12 (1H, s).

77. 1-(4-Dimethylaminophenyl)-3-(6-fluoroquinolin-4-yl)urea dihydrochloride

From D33 (0.191 g) and N,N-dimethylamino-1,4-benzenediamine (0.136 g) the title compound (0.065 g) was prepared to the method of Example 50.

¹H NMR δ: 3.08 (6H, s), 7.48–7.65 (4H, m), 8.08 (1H, m), 8.28 (1H, dd, J 5+9 Hz), 8.75 (1H, d, J 7 Hz), 9.02 (1H, d, J 7 Hz), 9.13 (1H, m), 11.20 (2H, s).

m/z (API⁺): 325 (MH⁺).

78. 1-(3,5-Dimethoxyphenyl)-3-quinolin-4-ylurea hydrochloride

D4 (0.14 g) and 3,5-dimethoxphenylisocyanate (0.179 g) were combined in dichloromethane (20 ml) and stirred for 16 h. Solvent was removed at reduced pressure, the residue dissolved in methanol and excess ethereal HCl added. The precipitated title compound (0.17 g) was collected by filtration.

¹H NMR δ: 3.75 (6H, s), 6.27 (1H, t, J 2.2 Hz), 6.79 (2H, d, J 2.2 Hz), 7.93 (1H, m), 8.08–8.18 (2H, m), 8.73 (1H, d, J 6.8 Hz), 8.98 (1H, d, J 6.8 Hz), 9.07 (1H, d, J 5 8.6 Hz), 10.97 (1H, s), 11.03 (1H, s).

m/z (API⁺): 324 (MH⁺).

79. 1-(4-Dimethylaminophenyl)-3-(8-acetylquinolin-4-yl)urea

From D29 (0.420 g) and N,N-dimethylamino-1,4-benzenediamine (0.27 g) the title compound (0.135 g) was prepared according to the method of Example 50.

¹H NMR δ: 2.76 (3H, s), 3.34 (6H, s), 6.74 (2H, d, J 9 Hz), 7.34 (2H, d, J 9 Hz), 7.75 (2H, m), 8.30 (2H, m), 8.76 (1H, d, J 9 Hz), 9.00 (1H, s), 9.24 (1H, s).

m/z (API⁺): 349 (MH⁺).

80. 1-(4-Dimethylaminophenyl)-3-[8-(1-hydroxyethyl)quinolin-4-yl]urea

To a solution of Example 79 (0.090 g) in ethanol/water (15 ml/5 ml) was added sodium borohydride (0.040 g). The mixture was stirred under argon at ambient temperature for 16 h. HCl (5M) was added dropwise with ice-cooling until effervesence ceased. The mixture was basified with saturated aqueous Na₂CO₃, the solvents removed at reduced pressure and the residue triturated with water. The resulting solid was collected by filtration, trituration with hot ethyl acetate gave the title compound (0.040 g).

¹H NMR δ: 1.44 (3H, d, J 6 Hz), 2.86 (6H, s), 5.33 (1H, bm), 5.81 (1H, bm), 6.74 (2H, d, J 9 Hz), 7.34 (2H, d, J 9 Hz), 7.64 (1H, dd, J 8+8 Hz), 7.88 (1H, d, J 8 Hz), 8.14 (1H, d, J 8 Hz), 8.23 (1H, d, J 5 Hz), 8.70 (1H, d, J 5 Hz), 9.16 (1H, s), 9.22 (1H, s).

m/z (API⁺): 350 (MH⁺).

81. 1-(4-Dimethylaminophenyl)-3-(8-carboxamidoquinolin-4-yl)urea

To a solution of Example 78 (0.115 g) in dimethylsulfoxide (12 ml) at 15° C. was added hydrogen peroxide in water (0.044 ml, 27.85 w/v) and K₂CO₃ (0.072 g). The reaction mixture was heated at 100° C. for 1 h, the dimethyl sulfoxide removed at reduced pressure and water added. The resulting solid was collected by filtration, trituration with methanol gave the title compound (0.050 g).

¹H NMR δ: 3.35 (6H, s), 6.75 (2H, d, J 9 Hz), 7.35 (2H, d, J 9 Hz), 7.78 (1H, dd, J 8+8 Hz), 7.89 (1H, bs), 8.35 (1H, d, J 5 Hz), 8.41 (1H, d, J 8 Hz), 8.59 (1H, d, J 8 Hz), 8.81 (1H, d, J 8 Hz), 9.04 (1H, s), 9.30 (1H, s), 10.48 (1H, bs).

m/z (API⁺): 350 (MH⁺).

82. 1-(2-Methylbenzoxazol-6-yl)-3-quinolin-4-ylurea hydrochloride

From 2-methyl-6-benzoxazole carboxylic acid (0.150 g) and D4 (0.14 g) the title compound (0.170 g) was prepared according to Example 1, Method 3.

¹H NMR (CD₃OD) δ: 2.62 (3H, s), 7.34 (1H, dd, J 2+8 Hz), 7.65 (1H, d, J 8 Hz), 8.00 (2H, m), 8.08 (1H, d, J 2 Hz), 8.16 (2H, m), 8.70 (2H, bs), 8.76 (1H, d, 7 Hz), 9.02 (1H, d, J 7 Hz).

m/z (API⁺): 319 (MH⁺).

83. 1-Benzoxazol-6-yl-3-quinolin-4-ylurea hydrochloride

From D30 (0.200 g) and D4 (0.14 g) the title compound (0.060 g) was prepared according to Example 1, Method 3.

1H NMR δ: 7.40 (1H, dd, J 2+9 Hz), 7.90 (1H, d, J 9 Hz), 7.96 (1H, m), 8.15 (3H, m), 8.73 (2H, m), 8.92 (1H, d, J 9 Hz), 9.03 (1H, d, J 7 Hz), 10.67 (1H, s), 10.92 (1H, s).

84. [3-(3-Quinolin-4-ylureidophenoxy]acetic acid ethyl ester

From D3 (0.13 g) and 3-aminophenoxyacetic acid ethyl ester (0.128 g) the title compound (0.036 g), after recrystallisation from methanol/ethyl acetate, was prepared according to Example 1, Method 1.

¹H NMR δ: 1.23 (3H, t, J 7.2 Hz), 4.19 (2H, q, J 7.2 Hz), 4.78 (2H, s), 6.60 (1H, dd, J 2.1+8.1 Hz), 7.22–7.28 (2H, m), 7.68 (1H, t, J 7.0 Hz), 7.78 (1H, t, J 6.9 Hz), 7.99 (1H, d, J 7.5 Hz).

m/z (API⁺): 366 (MH⁺).

85. 1-Quinolin-3-yl-3-quinolin-4-ylurea dihydrochloride

From 4-quinoline carboxylic acid (0.173 g) and 3-aminoquinoline (0.14 g) the title compound (0.055 g) was prepared according to Example 1, Method 3.

¹H NMR δ: 7.64–7.74 (2H, m), 7.95 (1H, m), 8.04–8.25 (4H, m), 8.72 (1H, d, J 2 Hz), 8.80 (1H, d, J 7 Hz), 9.08 (2H, m), 9.20 (1H, d, J 9 Hz), 11.40 (1H, s), 11.78 (1H, s).

m/z (API⁺): 315 (MH⁺).

86. 1-Benzoxazol-5-yl-3-quinolin-4-ylurea hydrochloride

From D31 (0.200 g) and D4 (0.17 g) the title compound (0.034 g) was prepared according to Example 1, Method 3.

¹H NMR δ: 7.48 (1H, dd, J 2+9 Hz), 7.78 (1H, d, J 9 Hz), 7.91 (1H, m), 8.15 (3H, m), 8.75 (2H, m), 9.00 (1H, d, J 7 Hz), 9.14 (1H, d, J 9 Hz), 11.48 (1H, s), 11.32 (1H, s).

m/z (API⁺): 304.

87. 1-(3-Isopropoxyphenyl)-3-quinolin-4-ylurea hydrochloride

From D3 (0.22 g) and 3-isopropoxyaniline (0.07g) the title compound (0.036 g), after recrystallisation from methanol/ethyl acetate, was prepared according to Example 1, Method 1.

¹H NMR δ: 1.29 (6H, d, J 6.0 Hz), 4.54–4.64 (1H, m), 6.67 (1H, dd, J 2.1+8.2 Hz), 7.06 (1H, d, J 8.3 Hz), 7.23–7.29 (2H, m), 7.92 (1H, t, J 7.0 Hz), 8.08–8.19 (2H, m), 8.73 (1H, d, J 6.8 Hz), 9.00 (1H, d, J 6.8 Hz), 9.13 (1H, d, J 8.6 Hz), 11.06 (1H, s), 11.10 (1H, s).

m/z (API⁺): 322 (MH⁺).

88. 1-(2-Methylbenzoxazol-6-yl)-3-(6-fluoroquinolin-4-yl)urea hydrochloride

From 2-methyl-6-aminobenzoxazole (0.148 g) and D33 (0.191 g) the title compound (0.125 g) isolated by filtration, trituration with hot methanol and conversion to the hydrochloride, was prepared according to Example 1, Method 3.

¹H NMR δ: 2.61 (3H, s), 7.31 (1H, dd, J 1.95+8.6 Hz), 7.64 (1H, d, J 8.5 Hz), 8.01–8.09 (2H, m), 8.23 (1H, dd, J 4.0+9.3 Hz), 8.72 (1H, d, J 6.6 Hz), 8.91 (1H, dd, J 2+11 Hz), 9.00 (1H, d, J 6.7 Hz), 10.90 (1H, s), 10.97 (1H, s).

m/z (API⁺): 337 (MH⁺).

89. 1-(4-Dimethylaminophenyl)-3-(8-fluoroquinolin-4-yl)urea hydrochloride

From N,N-dimethylbenzene-1,4-diamine (0.178 g) and 8-fluoroquinoline-4-carboxylic acid (0.25 g), the title compound (0.036 g), after column chromatography and conversion to the hydrochloride, was prepared according to Example 1, Method 3 using toluene/dimethylformamide (2:1) as solvent.

¹H NMR δ: 3.13 (6H, s), 7.58–7.82 (6H, m), 8.05 (1H, dd, J 4.6+8.6 Hz), 8.98–9.02 (2H, m), 9.73 (1H, s), 10.37 (1H, s).

m/z (API⁺): 325 (MH⁺).

90. 1-(4-Dimethylaminophenyl)-3-(7-fluoroquinolin-4-yl)urea hydrochloride

From N,N-dimethylbenzene-1,4-diamine (0.178 g) and 7-fluoroquinoline-4-carboxylic acid (0.25 g), the title compound (0.036 g) after column chromatography and conversion to the hydrochloride, was prepared according to Example 1, Method 3, using toluene in place of dimethylformamide as solvent.

¹H NMR δ: 3.09 (6H, s), 7.59–7.67 (4H, m), 7.85–7.93 (1H, m), 7.97 (1H, dd, J 2.5+9.2 Hz), 8.71 (1H, d, J 6.8 Hz), 9.00 (1H, d, J 6.8 Hz), 9.34 (1H, m), 11.40 (2H, bs).

m/z (API⁺): 325 (MH⁺).

91. 1-(3-Phenoxyphenyl)-3-quinolin-4-ylurea hydrochloride

From D4 (0.135 g) and 3-phenoxybenzoic acid (0.20 g), the title compound (0.105 g), after column chromatography (silca gel (20% ethyl acetate/hexane) conversion to the hydrochloride and recrystallisation from methanol, was prepared according to Example 1, Method 3 using toluene/dimethylformamide (2:1) in place of dimethylformamide as reaction solvent.

¹H NMR δ: 6.73 (1H, dd, J 1.7+6.2 Hz), 7.06 (2H, dd, J 0.7+6.3 Hz), 7.15–7.27 (2H, m), 7.35–7.46 (4H, m), 7.91 (1H, t, J 7.0 Hz), 8.08–8.17 (2H, m), 8.68 (1H, d, J 6.8 Hz), 8.97 (1H, d, J 6.8 Hz), 9.09 (1H, d, J 8.6 Hz), 11.09 (1H, s), 11.17 (1H, s).

m/z (API⁺): 356 (MH⁺).

92. 1-Quinolin-6-yl-3-quinolin-4-ylurea

From D4 (0.216 g) and 6-aminoquinoline (0.216 g) the title compound (0.06 g) after recrystallisation from methanol was prepared according to Example 1, Method 2.

¹H NMR δ: 7.50 (1H, dd, J 4.2+8.3 Hz), 7.69–7.87 (3H, m), 8.00–8.03 (2H, m), 8.23–8.35 (4H, m), 8.76–8.80 (2H, m), 9.43 (1H, s), 9.68 (1H, s).

m/z (API$^+$): 315 (MH$^+$).

93. 1-(3-Benzyloxyphenyl)-3-quinolin-4-ylurea hydrochloride

From D3 (0.135 g) and 3-benzyloxyaniline (0.136 g) the title compound (0.139 g), after trituration of the hydrochloride salt with hot methanol, was prepared according to Example 1, Method 1.

¹H NMR δ: 5.12 (2H, s), 6.77 (1H, dd, J 2.2+8.1 Hz), 7.10 (1H, d, J 7.9 Hz), 7.25–7.51 (7H, m), 7.91 (1H, m), 8.08–8.19 (2H, m), 8.73 (1H, d, J 6.8 Hz), 9.00 (1H, d, J 6.8 Hz), 9.12 (1H, d, J 8.6 Hz), 11.11 (2H, s).

m/z (API$^+$): 370(MH$^+$).

94. 1-(2,5-Dimethoxyphenyl)-3-quinolin-4-ylurea

From 2,5-dimethoxyphenyl isocyanate (0.090 g) and D4 (0.072 g) the title compound (0.071 g) was prepared according to the method of Example 15.

¹H NMR δ: 3.72 (3H, s), 3.88 (3H, s), 6.57 (1H, dd, J 3.0+8.8 Hz), 6.98 (1H, d, J 8.9 Hz), 7.66 (1H, m), 7.78 (1H, m), 7.91 (1H, d, J 3.1 Hz), 8.26 (1H, d, J 5.2 Hz), 8.34 (1H, d, J 7.7 Hz), 8.72 (1H, d, J 5.2 Hz), 9.16 (1H, s), 9.79 (1H, s).

m/z (API$^+$): 324 (MH$^+$).

95. 1-(3-Chloro-2-methoxyphenyl)-3-quinolin-4-ylurea

From 3-chloro-2-methoxyphenyl isocyanate (0.092 g) and D4 (0.072 g) the title compound (0.03 g), after trituration with pentane/diethyl ether and dichloromethane was prepared according to the method of Example 15.

¹H NMR δ: 3.87 (3H, s), 7.13–7.16 (2H, m), 7.69 (1H, t, J 6.9 Hz), 7.79 (1H, t, J 5.8 Hz), 7.99 (1H, d, J 8.3 Hz), 8.21–8.28 (2H, m), 8.32 (1H, d, J 7.6 Hz), 8.74 (1H, d, J 5.1 Hz), 9.37 (1H, s), 9.85 (1H, s).

m/z (API$^+$): 328, 330 (MH$^+$).

96. 1-(4-Dimethylaminophenyl-3-quinolin-4-ylthiourea dihydrochloride

To D4 (0.144 g) in dimethylformamide (8 ml) sodium hydride (0.05 g, 60% in oil) was added. The mixture was stirred for 30 min and 4-dimethylaminophenyl isothiocyanate (0.178 g) added. The mixture was stirred for 30 min, poured into water and extracted with ethyl acetate (3×50 ml). The combined organic phase was washed with water (2×50 ml), dried (Na$_2$SO$_4$), and solvent removed at reduced pressure. The residue was triturated with diethyl ether/hexane to give the title compound (0.22 g) as the free base which was converted to the dihydrochloride salt (0.235 g).

¹H NMR δ: 3.07 (6H, s), 7.42 (2H, bs), 7.77 (2H, d, J 8.1 Hz), 7.93 (1H, t, J 7.5 Hz), 8.14 (1H, t, J 7.0 Hz), 8.26 (1H, d, J 8.4 Hz), 9.02 (3H, m), 11.95 (1H, bs), 12.44 (1H, s).

m/z (API$^+$): 323 (MH$^+$).

97. 1-(1-Methyl-(1H)-indol-5-yl)-3-(6-methoxy)quinolin-4-ylurea

From 4-amino-6-methoxyquinoline (0.303 g) and 5-amino-1-methyl-(1H)-indole (0.255 g) the title compound (0.221 g), after column chromatography (silica gel, hexane→ethyl acetate) and trituration with diethyl ether, was prepared according to Example 1, Method 2.

¹H NMR δ: 3.96 (3H, s), 4.17 (3H, s), 6.57 (1H, d, J 2.9 Hz), 7.40 (1H, dd, J 1.9+8.8 Hz), 7.49 (1H, d, J 3.0 Hz), 7.57–7.64 (2H, m), 7.72 (1H, d, J 2.4 Hz), 7.98 (1H, d, J 1.7 Hz), 8.08 (1H, d, J 9.2 Hz), 8.38 (1H, d, J 5.1 Hz), 8.75 (1H, d, J 5.1 Hz), 9.17 (1H, bs), 9.26 (1H, bs).

m/z (API$^+$): 347 (MH$^+$).

98. 1-(3-Methoxyphenyl)-3-quinolin-4-ylurea

From D4 (0.072 g) and 3-methoxyphenyl isocyanate (0.075 g) the title compound (0.071 g), was prepared according to the method of Example 12

¹H NMR δ: 3.77 (3H, s), 6.62 (1H, dd, J 1.8 Hz+8.2 Hz), 6.97 (1H, d), 7.18–7.24 (2H, m), 7.63–7.68 (1H, m), 7.73–7.78 (1H, m), 7.98 (1H, d), 8.17–8.24 (2H, m), 8.74 (1H, d), 9.23 (1H, s), 9.31 (1H, s).

m/z (API$^+$): 294 (MH$^+$).

99. 1-[4-(5-Chloro-1,3-dioxo-1,3-dihydroisoindol-2-yl)-3-methylphenyl]-3-quinolin-4-yl urea hydrochloride From D4 (0.10 g) and N-(4-amino-2-methylphenyl-4-chlorophthalimide (0.199 g) the title compound (0.037 g), after column chromatography (silica gel, hexane→ethyl acetate) salt formation and recrystallisation from methanol, was prepared according to Example 1, Method 2.

¹H NMR δ: 2.15 (3H, s), 7.37 (1H, d, J 8.4 Hz), 7.54–7.60 (2H, m), 7.91–8.03 (3H, m), 8.08–8.19 (3H, m), 8.75 (1H, d, J 6.8 Hz), 9.01–9.08 (2H, m), 11.06 (2H, bs).

m/z (API$^+$): 457, 459 (MH$^+$).

100. 1-(3-Nitrophenyl)-3-quinolin-4-ylurea

From D4 (0.64 g) and 3-nitrophenyl isocyanate (0.729 g) the title compound (0.071 g), after trituration with hot ethanol, was prepared according to the method of Example 12.

¹H NMR δ: 7.59–7.85 (4H, m), 7.89 (1H, dd, J 1.4+8.1 Hz), 8.20–8.24 (2H, m), 8.65 (1H, m), 8.76 (1H, d, J 5.1 Hz), 9.37 (1H, s), 9.79 (1H, s).

m/z (API$^+$): 309 (MH$^+$).

101. 1-(3-Aminophenyl)-3-quinolin-4-ylurea 1-(3-Nitrophenyl)-3-quinolin-4-ylurea (0.775 g) was suspended in ethanol (150 ml) containing 10% Pd/C (0.75 g paste) and shaken under a hydrogen atmosphere (50 psi) at room temperature. After 3 h the mixture was filtered (celite pad) and the residue washed with ethanol. The combined filtrate and washings were evaporated to dryness under reduced pressure and the residue triturated with diethyl ether/hexane to give the title compound (0.54 g).

¹H NMR δ: 5.13 (2H, s), 6.26 (1H, d, J 7.8 Hz), 6.65 (1H, d, J 7.8 Hz), 6.83 (1H, s), 6.95 (1H, t, J 7.9 Hz), 7.67 (1H, t, J 7.0 Hz), 7.77 (1H, t, J 6.9 Hz), 7.97 (1H, d, J 8.0 Hz), 8.19–8.25 (2H, m), 8.71 (1H, d, J 5.2 Hz), 9.09 (1H, bs), 9.16 (1H, bs).

m/z (API$^+$): 279 (MH$^+$).

102. N-[3-(3-Quinolin-4-ylureido)phenyl]methanesulphonamide

Methanesulphonyl chloride (27 ul) was added to 1-(3-aminophenyl)-3-quinolin-4-ylurea (0.08 g) in dichloromethane (25 ml) containing triethylamine (48 ul) and stirred for 16 h. The precipitate that formed was separated by filtration, washed with tetrahydrofuran and diethyl ether and dried to give the title compound (0.081 g).

$^1$H NMR δ: 3.03 (3H, s), 6.93–6.98 (1H, m), 7.33–7.35 (2H, m), 7.52 (1H, s), 7.95 (1H, m), 8.04–8.14 (2H, m), 8.66 (1H, d), 8.75 (1H, d), 8.99 (1H, d), 9.86 (1H, s), 10.35 (1H, s), 10.55 (1H, s).

m/z (API$^+$): 357 (MH$^+$).

Determination of HFGAN72 Receptor Antagonist Activity

The HFGAN72 receptor antagonist activity of the compounds of formula (I), including those compounds in which X and Y both represent CH and without provisos a)–f), was determined in accordance with the following experimental method.

Experimental Method

HEK293 cells expressing the human HFGAN72 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 μl/well into 96-well black clear bottom sterile plates from Costar which had been pre-coated with 10 μg/well of poly-L-lysine from SIGMA. The seeded plates were incubated overnight at 37° C. in 5% $CO_2$.

Agonists were prepared as 1 mM stocks in water:DMSO (1:1). $EC_{50}$ values (the concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist $IC_{50}$ values (the concentration of compound needed to inhibit 50% of the agonist response) were determined against 3.0 nM human Lig 72A using 11× half log unit dilutions in Tyrode's buffer containing 10% DMSO and probenecid. On the day of assay 50 μl of cell medium containing probenecid (Sigma) and Fluo3AM (Texas Fluorescence Laboratories) was added (Quadra, Tomtec) to each well to give final concentrations of 2.5 mM and 4 μM, respectively. The 96-well plates were incubated for 90 min at 37° C. in 5% $CO_2$. The loading solution containing dye was then aspirated and cells were washed with 4×150 μl Tyrode's buffer containing probenecid and 0.1% gelatin (Denley Cell Wash). The volume of buffer left in each well was 125 μl. Antagonist or buffer (25 μl) was added (Quadra) the cell plates gently shaken and incubated at 37° C. in 5% $CO_2$ for 30 min. Cell plates were then transferred to the Fluorescent Imaging Plate Reader (FLIPR, Molecular Devices) instrument and maintained at 37° C. in humidified air. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of readings 1–19 inclusive was subtracted from this figure. The peak increase in fluorescence was plotted against compound concentration and iteratively curve fitted using a four parameter logistic fit (as described by Bowen and Jerman, 1995, TiPS, 16, 413–417) to generate a concentration effect value. Antagonist Kb values were calculated using the equation:

$$K_b = IC_{50}/(1+([3/EC_{50}])$$

where $EC_{50}$ was the potency of human Lig72A determined in the assay (in nM terms) and $IC_{50}$ is expressed in molar terms.

As an illustration of the activity of the compounds of formula (I), the compounds of Examples 1, 14, 17 and 31 each had a pKb>7 in this assay.

What is claimed is:

1. A compound of formula (I):

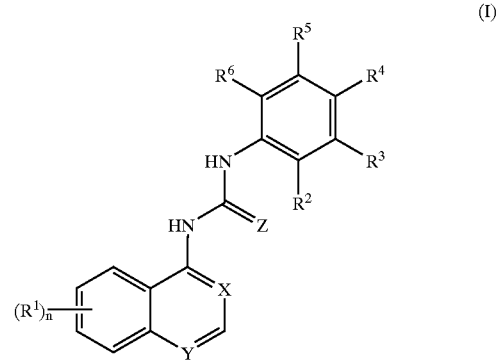

in which:

X and Y independently represent CH or nitrogen, provided that X and Y do not both represent CH;

Z represents oxygen or sulphur;

$R^1$ represents $(C_{1-6})$alkyl, $(C_{2-6})$alkenyl or $(C_{1-6})$alkoxy, any of which may be optionally substituted; halogen, $R^7CO$— or $NR^8R^9CO$—;

$R^2$, $R^3$, $R^4$, $R^5$ and $R^6$ independently represent $(C_{1-6})$alkyl, $(C_{2-6})$alkenyl, $(C_{1-6})$alkoxy or $(C_{1-6})$alkylthio, any of which may be optionally substituted; hydrogen, halogen, nitro, cyano, aryloxy, aryl($C_{1-6}$)alkyloxy, aryl($C_{1-6}$)alkyl, $R^7CO$—, $R^7SO_2NH$—, $R^7CON(R^{10})$—, $NR^8R^9$—, $NR^8R^9CO$—, —$COOR^8$ or heterocyclyl; provided that at least one of $R^2$, $R^3$, $R^4$, $R^5$ and $R^6$ is other than hydrogen;

or an adjacent pair of $R^2$, $R^3$, $R^4$, $R^5$ and $R^6$ together with the carbon atoms to which they are attached form an optionally substituted carbocyclic or heterocyclic ring;

$R^7$ is $(C_{1-6})$alkyl or aryl;

$R^8$ and $R^9$ independently represent hydrogen, $(C_{1-6})$alkyl, aryl or aryl($C_{1-6}$)alkyl;

$R^{10}$ is hydrogen or $(C_{1-6})$alkyl; and n is 0, 1, 2, 3 or 4;

or a pharmaceutically acceptable salt thereof;

provided that the compound is not:

a) N-1-isoquinolinyl-N'-(1-methyl-1H-indol-5-yl)urea;

b) N-(3-chloro-4-trifluoromethylphenyl)-N'-4-quinolinylurea;

c) N-(3-chloro-4-trifluoromethylphenyl)-N'-(5-nitro-4-quinolinyl)urea;

d) N-(3,4,5-trimethoxyphenyl)-N'-(7-chloro-4-quinolinyl)urea;

e) N-(4-methoxyphenyl)-N'-(7-chloro-4-quinolinyl)urea; or f) N-(4-chlorophenyl)-N'-(7-chloro-4-quinolinyl)urea.

2. A compound according to claim 1, in which X represents CH and Y represents nitrogen.

3. A compound according to claim 1, in which Z represents oxygen.

4. A compound according to claim 1, in which n is 0 or 1.

5. A compound according to claim 1, in which $R^2$ to $R^6$ independently represent hydrogen, halogen, $(C_{1-6})$alkoxy, $(C_{1-6})$alkylthio or $NR^8R^9$, and at least one of $R^2$ to $R^6$ is other than hydrogen; or an adjacent pair of $R^2$ to $R^6$ together with the carbon atoms to which they are attached form an optionally substituted 5- to 7-membered heterocyclic ring.

6. A compound according to claim 1 in which $R^2$, $R^5$ and $R^6$ represent hydrogen.

7. A compound according to claim 1 in which $R^2$, $R^4$ and $R^6$ represent hydrogen.

8. A compound according to claim 1 selected from: 1-(1-methyl-1H-indol-5-yl)-3-quinolin-4-ylurea, 1-(1-methyl-1H-indol-5-yl)-3-quinolin-4-yl)urea hydrochloride, 1-(1-ethyl-1H-indol-5-yl)-3-quinolin-4-ylurea, 1-[1-(3-phenylpropyl)-1H-indol-5-yl]-3-quinolin-4-ylurea, 1-(1-benzyl-1-H-indol-5-yl)-3-quinolin-4-ylurea, 1-[1-(3-carboethoxypropyl)-1H-indol-5-yl]-3-quinolin-4-ylurea, 1-[1-(3-cyanopropyl)-1H-indol-5-yl]-3-quinolin-4-ylurea hydrochloride, 1-(1H-indol-5-yl)-3-quinolin-4-ylurea, 1-(1-methyl-1H-indolin-5-yl)-3-quinolin-4-ylurea, 1-(1-methyl-1(1H-indolin-5-yl)-3-quinolin-4-ylurea dihydrochloride, 1-(2,3-dihydrobenzo[1,4]dioxin-6-yl)-3-quinolin-4-ylurea hydrochloride, 1-benzo[1,3]dioxol-5-yl-3-quinolin-4-ylurea hydrochloride, 1-(4-methoxyphenyl)-3-quinolin-4-ylurea, 1-(3-methylthiophenyl)-3-quinolin-4-ylurea hydrochloride, 1-(3,4-dimethoxyphenyl)-3-quinolin-4-ylurea, 1-(4-methylthiophenyl)-3-quinolin-4-ylurea hydrochloride, 1-(3-ethylphenyl)-3-quinolin-4-ylurea, 1-(4-ethoxyphenyl)-3-quinolin-4-ylurea, 1-(4-N,N-dimethylaminophenyl)-3-quinolin-4-ylurea, 1-(4-N,N-dimethylaminophenyl)-3-quinolin-4-ylurea dihydrochloride, 1-(4-carboethoxyphenyl)-3-quinolin-4-ylurea, 1-(4-n-butylphenyl)-3-quinolin-4-ylurea, 1-(4-ethylphenyl)-3-quinolin-4-ylurea, 1-(4-trifluoromethoxyphenyl)-3-quinolin-4-ylurea, 1-(4-chlorophenyl)-3-quinolin-4-ylurea, 1-(3-chlorophenyl)-3-quinolin-4-ylurea, 1-(3-chloro-4-methylphenyl)-3-quinolin-4-ylurea, 1-(3-cyanophenyl)-3-quinolin-4-ylurea, 1-(3,4-dichlorophenyl)-3-quinolin-4-ylurea, 1-(3-carboethoxyphenyl)-3-quinolin-4-ylurea hydrochloride, 1-(3-bromo-4-methoxyphenyl)-3-quinolin-4-ylurea hydrochloride, 1-(4-trifluoromethylthiophenyl)-3-quinolin-4-ylurea hydrochloride, 1-(8-oxo-5,6,7,8-tetrahydronaphthalen-2-yl)-3-quinolin-4-ylurea hydrochloride, 1-(3-chloro-4-methoxyphenyl)-3-quinolin-4-ylurea hydrochloride, 1-(4-N-morpholin-4-ylphenyl)-1-quinolin-4-ylurea dihydrochloride, 1-(3-acetylphenyl)-3-quinolin-4-ylurea hydrochloride, 1-(4-phenylaminophenyl)-3-quinolin-4-ylurea dihydrochloride, 1-[3-(1,3-oxazo-5-yl)phenyl]-3-quinolin-4-ylurea, 1-[4-((4,6-dimethylpyrimidin-2-yl)methylamino)phenyl]-3-quinolin-4-ylurea dihydrochloride, 1-(4-pyrrolidinylphenyl)-3-quinolin-4-ylurea dihydrochloride, 1-(3-dimethylaminophenyl)-3-quinolin-4-ylurea dihydrochloride, 1-(4-carboxamidophenyl)-3-quinolin-4-ylurea hydrochloride, 1-(4-N,N-diethylaminophenyl)-3-quinolin4-ylurea dihydrochloride, 1-(4-dimethylaminophenyl)-3-(5-methoxyquinolin-4-yl)urea dihydrochloride, 1-(4-dimethylaminophenyl)-3-(8-bromoquinolin-4-yl)urea dihydrochloride, 1-(4-dimethylaminophenyl)-3-(8-methoxyquinolin-4-yl)urea dihydrochloride, 1-(2-chlorophenyl)-3-quinolin-4-ylurea, 1-(2-methylphenyl)-3-quinolin-4-ylurea, 1-(4-methoxy-2-methylphenyl)-3-quinolin-4-ylurea hydrochloride, 1-(1-hydroxy-1-ethylphen-3-yl)-3-quinolin-4-ylurea hydrochloride, 1-(3-trifluoromethylthiophenyl)-3-quinolin-4-ylurea hydrochloride, 1-(3,5-dichlorophenyl)-3-quinolin-4-ylurea hydrochloride, 1-(1-methylbenzimidazol-6-yl)-3-quinolin-4-ylurea dihydrochloride, 1-(4-methoxy-3-trifluoromethylphenyl)-3-quinolin-4-ylurea hydrochloride, N-methyl-3-(3-quinolin-4-ylureido)benzamide hydrochloride, 1-(4-dimethylaminomethylphenyl)-3-quinolin-4-ylurea dihydrochloride, 1-(4-hydroxymethylphenyl)-3-quinolin-4-ylurea hydrochloride, 1-(4-N,N-dimethylaminophenyl)-3-(7-methoxy)quinolin-4-ylurea hydrochloride, 1-(3-fluoro-4-methoxyphenyl)-3-quinolin-4-ylurea hydrochloride, 1-(3,4-dihydro-2H-benzo[b][1,4]dioxepin-7-yl)-3-quinolin-4-ylurea hydrochloride, 1-(3-chloro-4-dimethylaminophenyl)-3-quinolin-4-ylurea dihydrochloride, 1-quinolin-4-yl-3-(4-[1,2,4]triazol-1-ylphenyl) urea hydrochloride, 1-(benzothiazol-6-yl)-3-quinolin-4-ylurea hydrochloride, 1-benzo[b]thiophen-5-yl-3-quinolin-4-ylurea hydrochloride, 1-(1-methyl-1,2,3,4-tetrahydroquinolin-6-yl)-3-quinolin-4-ylurea dihydrochloride, 1-(4-N-ethyl-N-isopropylaminophenyl)-3-quinolin-4-ylurea dihydrochloride, 1-(4-methyl-3,4-dihydro-2H-benzo[1,4]oxazin-7-yl)-3-quinolin-4-ylurea dihydrochloride, 1-(2-methyl-1,2,3,4-tetrahydro-isoquinolin-7-yl)-3-quinolin-4-yl urea hydrochloride, 1-(1,2-dimethyl-1H-indol-5-yl)-3-quinolin-4-ylurea hydrochloride, 1-(2,3-dihydro-1H-indol-5-yl)-3-quinolin-4-yl urea dihydrochloride, 1-(4-dimethylaminophenyl)-3-(7-bromoquinolin-4-yl)urea dihydrochloride, 1-(4-dimethylaminophenyl)-3-(6-bromoquinolin-4-yl)urea dihydrochloride, 1-(3-ethoxyphenyl)-3-quinolin-4-ylurea hydrochloride, 1-(4-ethylthiophenyl)-3-quinolin-4-yl urea hydrochloride, 1-(3-bromo-4-dimethylaminophenyl)-3-quinolin-4-ylurea-dihydrochloride, 1-(4-methoxy-3-methylphenyl)-3-quinolin-4-ylurea hydrochloride, 1-(4-methoxy-3-prop-2-enylphenyl)-3-quinolin-4-yl hydrochloride, 1-(3-ethyl-4-methoxyphenyl)-3-quinolin-4-ylurea hydrochloride, 1-(3-acetyl-4-methoxyphenyl)-3-quinolin-4-ylurea hydrochloride, 1-(4-dimethylaminophenyl)-3-(6-fluoroquinolin-4-yl)urea dihydrochloride, 1-(3,5-dimethoxyphenyl)-3-quinolin-4-ylurea hydrochloride, 1-(4-dimethylaminophenyl)-3-(8-acetylquinolin-4-yl)urea, 1-(4-dimethylaminophenyl)-3-[8-(1-hydroxyethyl)quinolin-4-yl]urea, 1-(4-dimethylaminophenyl)-3-(8-carboxamidoquinolin-4-yl)urea, 1-(2-methylbenzoxazol-6-yl)-3-quinolin-4-ylurea hydrochloride, 1-benzoxazol-6-yl-3-quinolin-4-ylurea hydrochloride, [3-(3-quinolin-4-ylureidophenoxy]acetic acid ethyl ester, 1-quinolin-3-yl-3-quinolin-4-ylurea dihydrochloride, 1-benzoxazol-5-yl-3-quinolin-4-ylurea hydrochloride, 1-(3-isopropoxyphenyl)-3-quinolin-4-ylurea hydrochloride, 1-(2-methylbenzoxazol-6-yl)-3-(6-fluoroquinolin-4-yl)urea hydrochloride, 1-(4-dimethylaminophenyl)-3-(8-fluoroquinolin-4-yl)urea hydrochloride, 1-(4-dimethylaminophenyl)-3-(7-fluoroquinolin-4-yl)urea hydrochloride, 1-(3-phenoxyphenyl)-3-quinolin-4-ylurea hydrochloride, 1-quinolin-6-yl-3-quinolin-4-ylurea, 1-(3-benzyloxyphenyl)-3-quinolin-4-ylurea hydrochloride, 1-(2,5-dimethoxyphenyl)-3-quinolin-4-ylurea, 1-(3-chloro-2-methoxyphenyl)-3-quinolin-4-ylurea, 1-(4-dimethylaminophenyl)-3-quinolin-4-ylthiourea dihydrochloride, 1-(1-methyl-(1H)-indol-5-yl)-3-(6-methoxy)quinolin-4-ylurea, 1-(3-methoxyphenyl)-3-quinolin-4-ylurea, 1-[4-(5-chloro-1,3-dioxo-1,3-dihydroisoindol-2-yl)-3-methylphenyl]-3-quinolin-4-yl urea hydrochloride, 1-(3-nitrophenyl)-3-quinolin-4-ylurea, 1-(3-aminophenyl)-3-quinolin-4-ylurea, and N-[3-(3-quinolin-4-ylureido)phenyl]methanesulphonamide.

9. A process for the preparation of a compound of formula (I) as defined in claim 1 or a salt thereof which comprises coupling a compound of formula (II):

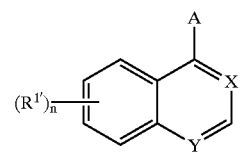

(II)

with a compound of formula (III):

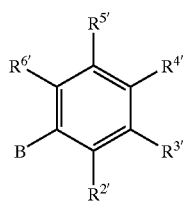

where A and B are appropriate functional groups to form the —NHCONH— or —NHCSNH— moiety when coupled; X, Y and n are as defined in formula (I); and $R^{1'}$ to $R^{6'}$ are $R^1$ to $R^6$ as defined in formula (I) or groups convertible thereto; and thereafter optionally and as necessary and in any appropriate order, converting any $R^{1'}$ to $R^{6'}$ when other than $R^1$ to $R^6$ respectively to $R^1$ to $R^6$, and/or forming a pharmaceutically acceptable salt thereof.

10. A pharmaceutical composition comprising a compound of formula (I) as defined in claim 1 or a pharmaceutically acceptable salt thereof and a pharmaceutically acceptable carrier.

11. A method of treating or preventing diseases or disorders where an antagonist of the human HFGAN72 receptor is required, which comprises administering to a subject in need thereof an effective amount of a compound of formula (I), according to claim 1, or a pharmaceutically acceptable salt thereof.

12. A method of treating or preventing diseases or disorders where an antagonist of the human HFGAN72 receptor is required, which comprises administering to a subject in need thereof an effective amount of a compound of formula (I) according to claim 8.

* * * * *